(12) United States Patent
Houben et al.

(10) Patent No.: US 10,136,828 B2
(45) Date of Patent: Nov. 27, 2018

(54) MAPPING OF ATRIAL FIBRILLATION

(71) Applicant: BIOSENSE WEBSTER (ISRAEL) LTD., Yokneam (IL)

(72) Inventors: Richard P. M. Houben, Lanaken (BE); Meir Bar-Tal, Haifa (IL); Yaniv Ben Zriham, Binyamina (IL); Roy Urman, Karkur (IL); Shmuel Auerbach, Kerem Maharal (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 52 days.

(21) Appl. No.: 15/086,220

(22) Filed: Mar. 31, 2016

(65) Prior Publication Data
US 2017/0281031 A1 Oct. 5, 2017

(51) Int. Cl.
| | |
|---|---|
| *A61B 18/12* | (2006.01) |
| *A61B 5/04* | (2006.01) |
| *A61B 5/042* | (2006.01) |
| *A61B 18/14* | (2006.01) |
| *A61B 5/044* | (2006.01) |
| *A61B 18/00* | (2006.01) |
| *A61B 5/00* | (2006.01) |
| *A61B 5/0452* | (2006.01) |

(52) U.S. Cl.
CPC ............ *A61B 5/0422* (2013.01); *A61B 5/044* (2013.01); *A61B 18/12* (2013.01); *A61B 18/1206* (2013.01); *A61B 18/1492* (2013.01); *A61B 5/0044* (2013.01); *A61B 5/04011* (2013.01); *A61B 5/0452* (2013.01); *A61B 5/4836* (2013.01); *A61B 5/743* (2013.01); *A61B 2018/00351* (2013.01); *A61B 2018/00636* (2013.01)

(58) Field of Classification Search
CPC .... A61B 5/04012; A61B 5/0422; A61B 18/12
See application file for complete search history.

(56) References Cited

U.S. PATENT DOCUMENTS

| | | | |
|---|---|---|---|
| 5,487,391 A * | 1/1996 | Panescu | ............... A61B 5/0538 600/374 |
| 6,226,542 B1 | 5/2001 | Reisfeld | |
| 6,301,496 B1 | 10/2001 | Reisfeld | |
| 6,814,733 B2 | 11/2004 | Schwartz et al. | |
| 6,892,091 B1 | 5/2005 | Ben-Haim et al. | |
| 6,997,924 B2 | 2/2006 | Schwartz et al. | |

(Continued)

OTHER PUBLICATIONS

U.S. Appl. No. 14/693,042, filed Apr. 22, 2015.
(Continued)

*Primary Examiner* — Allen Porter, Jr.
(74) *Attorney, Agent, or Firm* — Lewis Roca Rothgerber Christie LLP

(57) ABSTRACT

Electroanatomic mapping is carried out by inserting a multi-electrode probe into a heart of a living subject, recording electrograms from the electrodes concurrently at respective locations in the heart, delimiting respective activation time intervals in the electrograms, generating a map of electrical propagation waves from the activation time intervals, maximizing coherence of the waves by adjusting local activation times within the activation time intervals of the electrograms, and reporting the adjusted local activation times.

24 Claims, 25 Drawing Sheets

(56) References Cited

U.S. PATENT DOCUMENTS

| | | |
|---|---|---|
| 7,156,816 B2 | 1/2007 | Schwartz et al. |
| 7,536,218 B2 | 5/2009 | Govari et al. |
| 7,756,218 B2 | 7/2010 | Nakahara et al. |
| 8,428,700 B2 | 4/2013 | Harlev et al. |
| 8,478,383 B2 | 7/2013 | Bar-Tal et al. |
| 2008/0194979 A1* | 8/2008 | Madry ............... A61B 5/02405 600/523 |
| 2013/0324871 A1 | 12/2013 | Dubois et al. |
| 2014/0066787 A1 | 3/2014 | Narayan et al. |
| 2014/0176531 A1 | 6/2014 | Rubinstein et al. |
| 2014/0200572 A1 | 7/2014 | Spector |
| 2014/0228696 A1 | 8/2014 | Narayan et al. |
| 2015/0289807 A1 | 10/2015 | Narayan et al. |
| 2016/0045123 A1 | 2/2016 | Bar-Tal et al. |
| 2016/0051160 A1 | 2/2016 | Harlev et al. |
| 2016/0166167 A1* | 6/2016 | Narayan ............... A61B 5/042 600/510 |
| 2017/0172508 A1* | 6/2017 | Hultz ............... A61B 5/0422 |

OTHER PUBLICATIONS

U.S. Appl. No. 15/009,285, filed Jan. 28, 2016.

Auricchio, Angelo, M.D. et al., "Characterization of Left Ventricular Activation in Patients With Heart Failure and Left Bundle-Branch Block", Circulation, 2004, pp. 1133-1139, 109.

Fitzgerald, T.N. et al., "Estimation of Cardiac Conduction Velocities Using Small Data Sets", Computers in Cardiology, 2001, pp. 13-16, 28.

European Search Report dated Aug. 17, 2017 in corresponding European Patent Application No. 17163766.3.

Auricchio, et al., Characterization of Left Ventricular Activation in Patients With Heart Failure and Left Bundle-Branch Block, *Circulation*, Mar. 9, 2004, pp. 1133-1139.

Fitzgerald, et al., Estimation of Cardiac Conduction Velocities Using Small Data Sets, *Computers in Cardiology* 2001, vol. 28, pp. 13-16.

\* cited by examiner

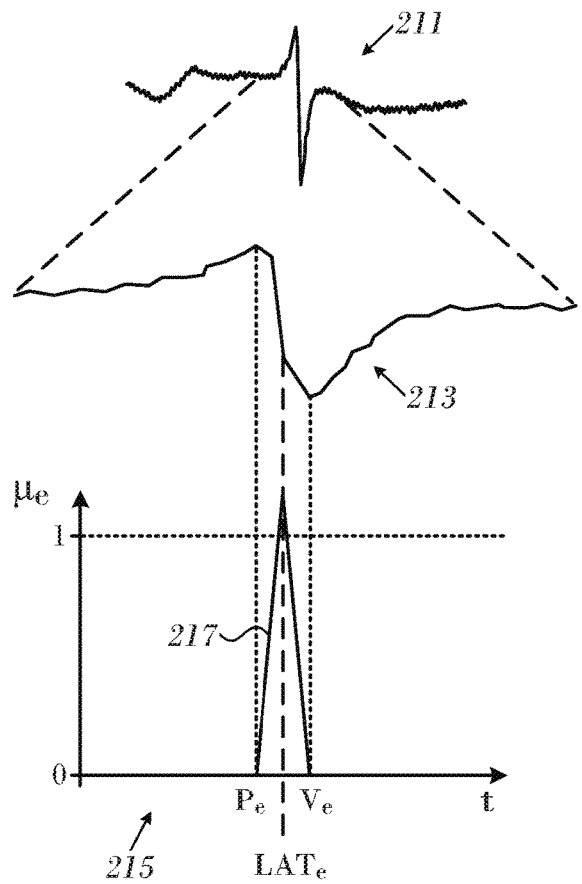
*FIG. 21*
*FIG. 22*
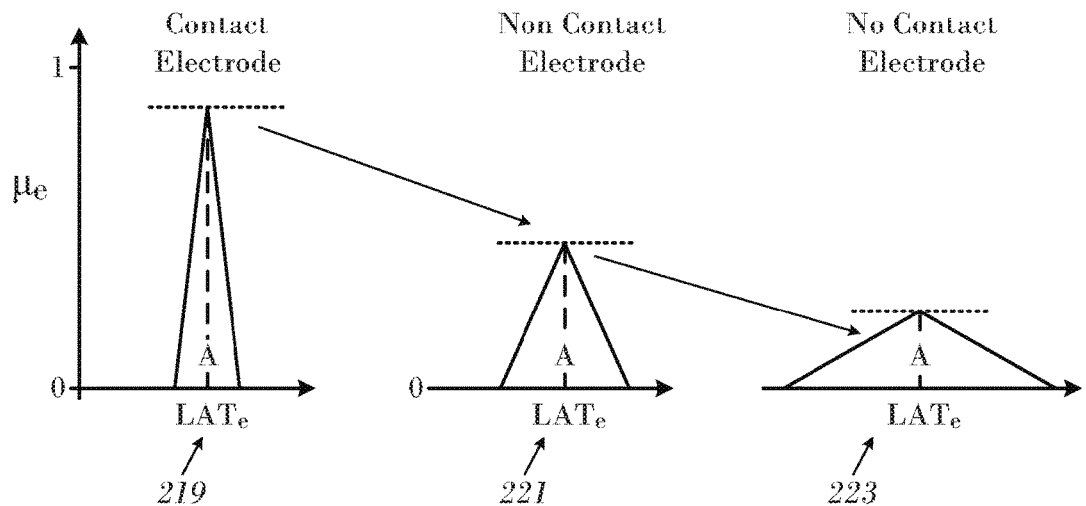

MAPPING OF ATRIAL FIBRILLATION

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to detecting, measuring or recording bioelectric signals of the body. More particularly, this invention relates to generation of electroanatomic maps relating to cardiac arrhythmias.

2. Description of the Related Art

TABLE 1

| Acronyms and Abbreviations | |
|---|---|
| CoG | Center of Gravity |
| CV | Conduction Velocity |
| ECG | Electrocardiogram |
| EGM | Electrogram |
| IC-EGM | Intracardiac Electrograms |
| LAT | Local Activation Time |
| MRI | Magnetic Resonance Imaging |

3-dimensional images of internal organs are useful in many catheter-based diagnostic and therapeutic applications, and real-time imaging is widely used during surgical procedures.

Mapping of electrical potentials in the heart is now commonly performed, using cardiac catheters comprising electrophysiological sensors for mapping the electrical activity of the heart. Typically, time-varying electrical potentials in the endocardium are sensed and recorded as a function of position inside the heart, and then used to map a local electrogram or local activation time. Activation time differs from point to point in the endocardium due to the time required for conduction of electrical impulses through the heart muscle. The direction of this electrical conduction at any point in the heart is conventionally represented by an activation vector, also referred to herein as a conduction velocity vector, which is normal to an isoelectric activation front, both of which may be derived from a map of activation time. The rate of propagation of the activation front through any point in the endocardium may be represented as a conduction velocity vector.

Localized defects in the heart's conduction of activation signals may be identified by observing phenomena such as multiple activation fronts, abnormal concentrations of activation vectors, or changes in the velocity vector or deviation of the vector from normal values. Examples of such defects include re-entrant areas, which may be associated with signal patterns known as complex fractionated electrograms. Once a defect is located by such mapping, it may be ablated if it is functioning abnormally or otherwise treated to restore the normal function of the heart insofar as is possible.

The document *Characterization of Left Ventricular Activation in Patients With Heart Failure and Left Bundle-Branch Block*, Auricchio et al., Circulation. 2004; 109:1133-1139 describes left ventricular activation sequences in patients with heart failure and left bundle block QRS morphology with simultaneous application of 3-dimensional contact and noncontact mapping during intrinsic rhythm and asynchronous pacing. A "U-shaped" activation wave front was present in most of the patients because of a line of block that was located anteriorly, laterally, or inferiorly. Functional behavior of the line of block was demonstrated by a change in its location during asynchronous ventricular pacing at different sites and cycle length.

SUMMARY OF THE INVENTION

Embodiments of the invention provide methods and systems for electroanatomic mapping in atrial fibrillation by simultaneous measurements of intracardiac electrograms within a defined area. The activation time is based on the full negative slope of a unipolar electrogram, rather than to a single fiducial point on the slope, e.g., maximum slope (maximum $-dV/dt$), mid-amplitude or time. Instead, a LAT range is determined for each of the slopes representing local activation. The LAT range is demarcated by a peak and valley representing the start and end of the slope, respectively, defining a time-window in which the activation wave passes.

Alternate embodiments of the invention further provide for identification of alternate activation periods preceding or following the slope, thereby accommodating short and long double potentials.

There is provided according to embodiments of the invention a method, which is carried out by inserting a multi-electrode probe into a heart of a living subject, recording electrograms from the electrodes concurrently at respective locations in the heart, delimiting respective activation time intervals in the electrograms, generating a map of electrical propagation waves from the activation time intervals, maximizing coherence of the waves by adjusting local activation times within the activation time intervals of the electrograms, and reporting the adjusted local activation times.

An aspect of the method includes ablating tissue in the heart to modify the waves.

According to an additional aspect of the method, the activation time intervals comprise first intervals delimited by a peak and a valley representing a start and an end of a slope and second intervals including windows about the first intervals, wherein adjusting local activation times is performed within the second intervals.

According to another aspect of the method, the windows about the first intervals are ±40 ms.

According to one aspect of the method, the local activation times at the respective locations of the electrodes are represented as fuzzy electrode membership functions ($\mu_e$) that vary from 0 to 1.

According to one aspect of the method, generating the map of electrical propagation waves includes segmenting the electrograms into a series of frames at respective times, wherein the frames are respective assignments of readings of the electrodes to a matrix of values.

Yet another aspect of the method includes assigning local activation times for the electrodes from the matrix of values, modeling at least a portion of the heart as a mesh, wherein a portion of the vertices in the mesh correspond to the respective locations of the electrodes, determining conduction velocities of electrical propagation between the vertices from the frames based on the assigned local activation times, and computing the coherence of the waves using the conduction velocities.

According to a further aspect of the method, maximizing coherence of the waves includes representing the conduction velocities as conduction velocity vectors, computing a velocity deviation vector at respective vertices from the conduction velocity vectors, and minimizing a length of the velocity deviation vector.

Still another aspect of the method includes interpolating activation times of vertices on the mesh that do not correspond to the respective locations of the electrodes.

According to a further aspect of the method, activation times at the vertices of the mesh are represented as fuzzy vertex membership functions ($\mu_u$) that vary between 0 and 1, the vertex membership functions at each of the vertices including weighted combinations of the vertex membership functions of neighboring vertices thereof.

According to yet another aspect of the method, maximizing coherence of the waves includes adjusting the activation times at the vertices of the mesh to maximize an average value of the vertex membership functions in the mesh.

Still another aspect of the method includes assigning vertex membership functions to non-neighboring vertices of the mesh by extrapolation.

There is further provided according to embodiments of the invention an apparatus, including a multi-electrode probe adapted for insertion into a heart of a living subject, and a processor, which is configured to receive an electrical signal from the electrodes and to perform the steps of recording electrograms from the electrodes concurrently at respective locations in the heart, delimiting respective activation time intervals in the electrograms, generating a map of electrical propagation waves from the activation time intervals, maximizing coherence of the waves by adjusting local activation times within the activation time intervals of the electrograms, and reporting the adjusted local activation times.

The apparatus may include an ablation power generator connected to the probe for ablating tissue in the heart to modify the waves.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein:

FIG. 2 is a set of unipolar LATs in atrial fibrillation that was prepared in accordance with an embodiment of the invention;

FIG. 7 is an exemplary frame segmentation map in accordance with an embodiment of the invention;

FIG. 21 is a composite diagram relating fuzzy LATs to the morphology of an intracardiac electrogram in accordance with an embodiment of the invention;

FIG. 22 is a series of plots of the function $\mu_e$ for electrodes at different distances from the endocardium in accordance with an embodiment of the invention;

DETAILED DESCRIPTION OF THE INVENTION

Figure 1:
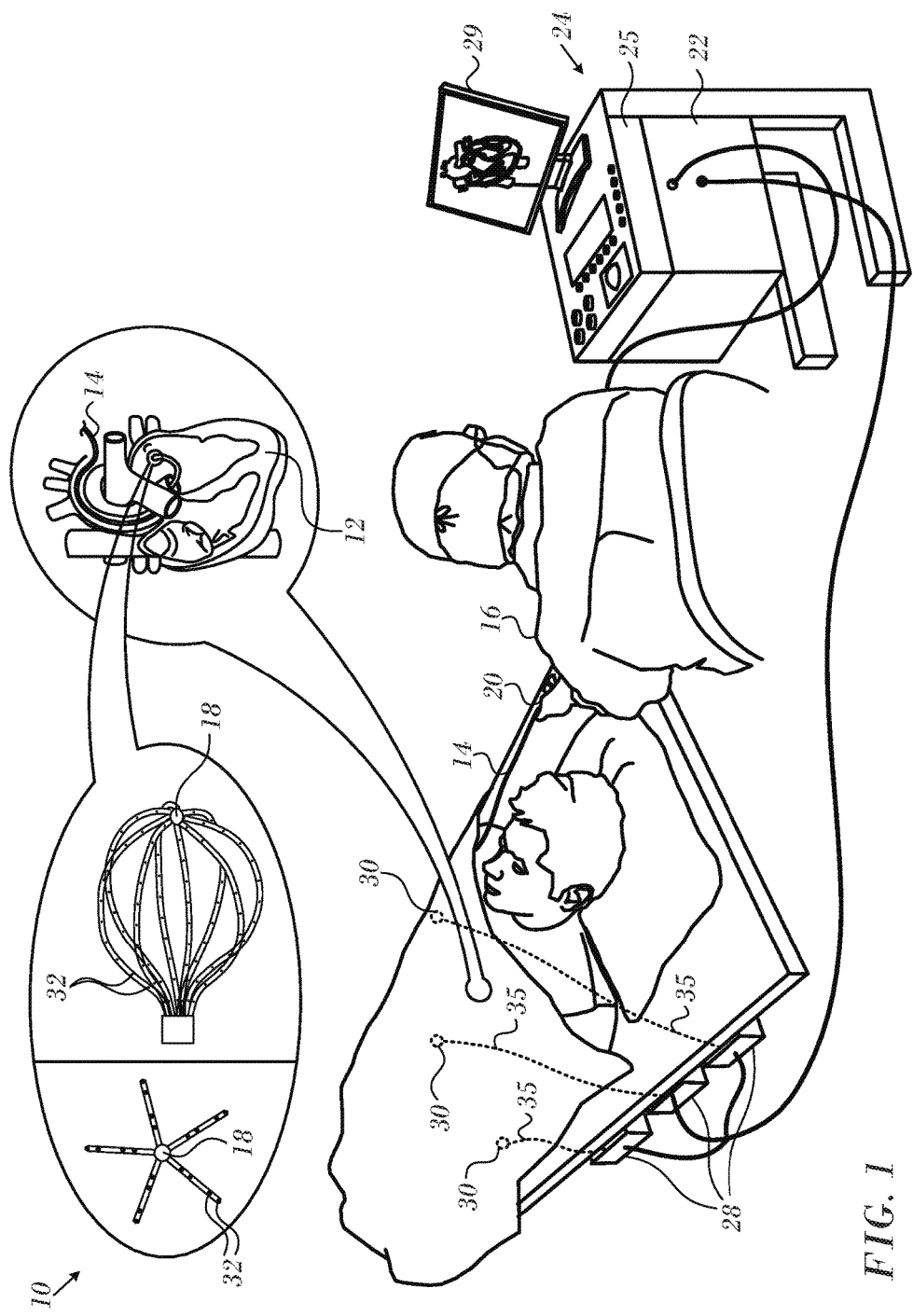
FIG. 1 is a pictorial illustration of a system for evaluating electrical activity in a heart of a living subject in accordance with an embodiment of the invention.

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Definitions.

"Annotations" or "annotation points" refer to points or candidates on an electrogram that are considered to denote events of interest. In this disclosure the events are typically local activation time of the propagation of an electrical wave as sensed by the electrode.

"Activity" in an electrogram is used herein to denote a distinct region of bursty or undulating changes in an electrogram signal. Such a region may be recognized as being outstanding between regions of baseline signals. In this disclosure "activity" more often refers to a manifestation on an electrogram of one or more electrical propagation waves through the heart.

A "wave" refers to continuous electrical propagation in the heart.

"Coherence" of a propagating electrical waves in the heart refers to a metric of the constancy of the phase and the equality of the frequency of the waves at different points in space or time.

A "line of block" refers to an impediment or block of electrical propagation in the heart. Such lines may demarcate waves. Waves may themselves contain lines of block, known as "intrawave blocks".

A "primary slope" of an electrogram is a slope related to a local activation time of an activation wave passing under the electrode A "secondary slope" is a slope related to a wave not passing under the electrode, i.e., from a distal activation wave, such as far-field activity.

A slope is "coupled" to another slope when both the slope and the other slope consistently occur within a defined time window A "block point" is a point, having a conduction velocity of less than a user-defined value, typically 0.2 m/s. Additionally or alternatively, a block point is a point located between two electrodes wherein an activation wave departing the first electrode arrives at the second electrode to find that the second electrode was previously activated within a user-defined time interval, e.g., 100 ms, immediately prior to the arrival, and after the beginning of the refractory period of the second electrode.

A "line of block" or "block line" is a collection of block points.

A "frame" is an assignment of concurrent individual readings of a mesh of electrode readings to a matrix of values.

A "neighbor" of an electrode or a vertex on a mesh surface refers to other electrodes or vertices on the surface in a 3×3 grid centered on the electrode or vertex.

Overview.

Turning now to the drawings, reference is initially made to FIG. 1, which is a pictorial illustration of a system 10 for performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference.

The system 10 may comprise a general purpose or embedded computer processor, which is programmed with suitable software for carrying out the functions described hereinbelow. Thus, although portions of the system 10 shown in other drawing figures herein are shown as comprising a number of separate functional blocks, these blocks are not necessarily separate physical entities, but rather may represent, for example, different computing tasks or data objects stored in a memory that is accessible to the processor. These tasks may be carried out in software running on a single processor, or on multiple processors. The software may be provided to the processor or processors on tangible non-transitory media, such as CD-ROM or non-volatile memory. Alternatively or additionally, the system 10 may comprise a digital signal processor or hard-wired logic. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

The catheter 14 is a multi-electrode catheter, which can be a basket catheter as shown in the right portion of balloon 37, or a spline catheter as shown in the left portion. In any case there are multiple electrodes 32, which are used as sensing electrodes and have known locations on the basket or spline, and known relationships to one another. Thus, once the catheter is located in the heart, for example by constructing a current position map, the location of each of the electrodes 32 in the heart is known. One method for generation of a current position map is described in commonly assigned U.S. Pat. No. 8,478,383 to Bar-Tal et al., which is herein incorporated by reference.

Electrical signals can be conveyed to and from the heart 12 from the electrodes 32 located at or near the distal tip 18 of the catheter 14 via cable 34 to the console 24. Pacing signals and other control signals may be conveyed from the console 24 through the cable 34 and the electrodes 32 to the heart 12.

Wire connections 35 link the console 24 with body surface electrodes 30 and other components of a positioning sub-system for measuring location and orientation coordinates of the catheter 14. The processor 22, or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted near the distal tip 18 of the catheter 14.

The console 24 typically contains one or more ablation power generators 25. The catheter 14 may be adapted to conduct ablative energy to the heart using any known ablation technique, e.g., radiofrequency energy, ultra-sound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. A suitable positioning subsystem is described in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14 and to analyze the electrical signals from the electrodes as described in further detail below.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally applied reference patch attached to the exterior of the subject's body, or on an internally-placed catheter, which is inserted into the heart 12 and maintained in a fixed position relative to the heart 12. The system 10 may receive image data from an external imaging modality, such as an MRI unit or the like and includes image processors that can be incorporated in or invoked by the processor 22 for generating and displaying images that are described below.

Mapping in Atrial Fibrillation.

Atrial fibrillation is characterized by a complex pattern of propagation, without periodic or repetitive patterns. There may be multiple lines of block, separating various forms of dissociated waves. Attempts to map atrial activation times to an atrial electrode mesh result in measurement errors. Spatial resolution based on electrode readings from a mapping catheter is inadequate for evaluating complex atrial fibrillation activation patterns.

Several steps need to be taken to produce trustworthy electroanatomic maps that reconstruct the activation of the mapped area in atrial fibrillation. These steps typically include preprocessing of the acquired electrograms, detection of local activation times, followed by combining LATs related to activation of tissue underneath the various electrodes on the mapping array into an interpretable map or movie.

One approach to wave mapping is described in commonly assigned U.S. Patent Publication No. 2016/0045123, entitled Line of Block Detection, which is herein incorporated by reference. The procedures described therein detect and map atrial waves within a context of frames, i.e., frame segmentation. These procedures are particularly useful for mapping waves that are delineated by lines of block.

Figure 2:
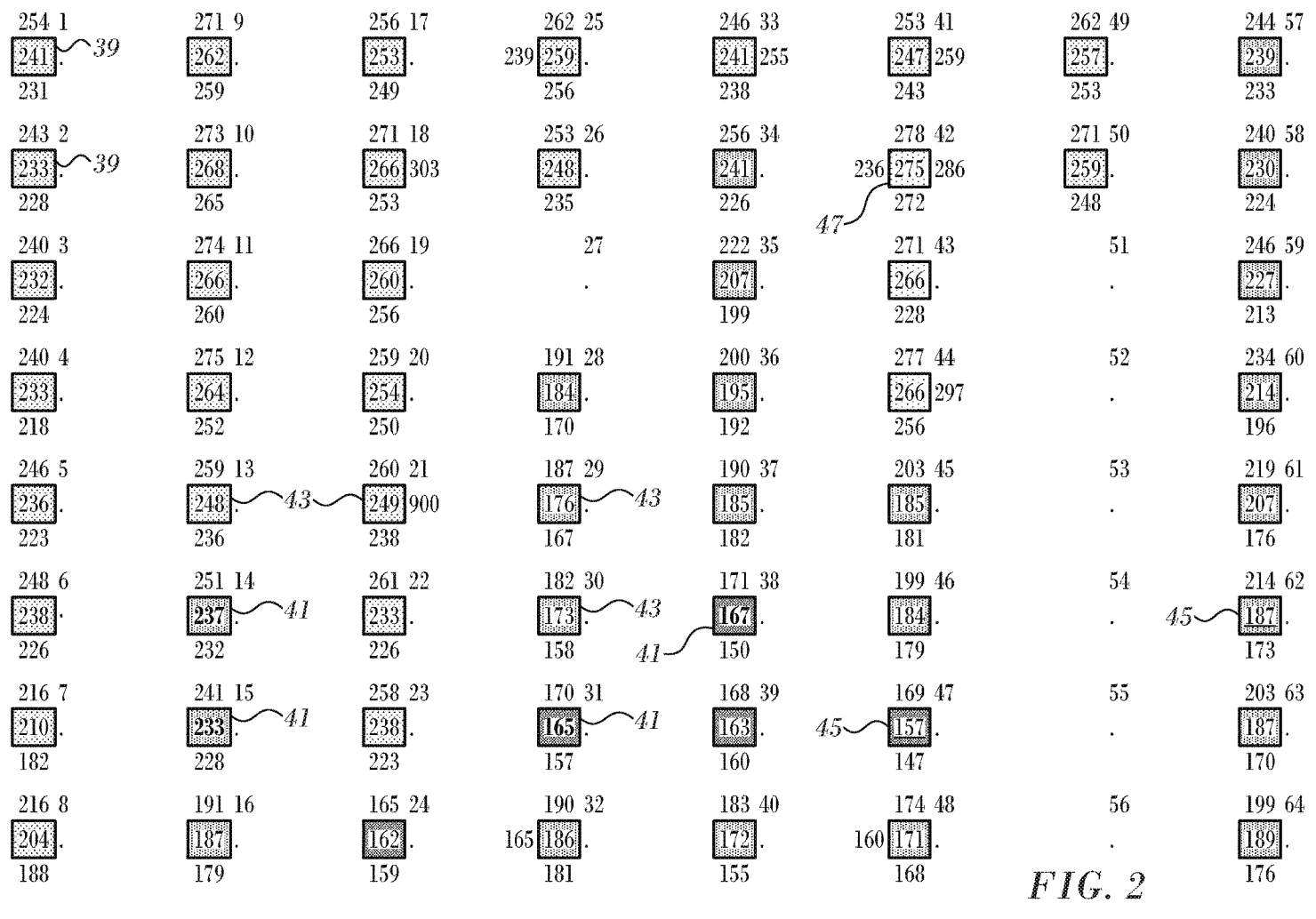

According to embodiments of the invention, the activation time is based on the full negative slope of a unipolar electrogram, rather than to a single fiducial point on the slope, e.g., maximum slope (maximum $-dV/dt$), mid-amplitude or time. Instead, a LAT range is determined for each of the slopes representing local activation. This LAT range is demarcated by a peak and the valley representing the start and end of the slope, defining a time window in which the activation wave passes Reference is now made to FIG. 2, which is a set of unipolar LATs in atrial fibrillation that was prepared in accordance with an embodiment of the invention. The values derive from readings produced by an endocardial mapping catheter having 64 (8×8) electrodes, in accordance with an embodiment of the invention. In this presentation, each square is identified by a position number 39 (varying from 1-64) at the right upper corner. Squares 41 show unipolar LATs in bold font that were generally obtained from the maximum negative slope (dV/dt) and are trusted. These are fixed, and cannot be changed. Squares 43 show LATs in normal font that fall within a LAT time window having upper and lower limits shown respectively above and below the squares. These limits are derived from the time incidence of the peak and valley demarcating the slope on which the LAT is defined (maximum $-dV/dt$). They precede and follow the LAT and are determined before the algorithms described below are executed. Within these limits the values in squares 45 can be changed by the algorithm described below. Squares 45 having numbers in underlined font are untrustworthy. Positions on the grid lacking squares also represent unreliable readings. In some cases, e.g., square 47, alternative upper and lower limits of the LAT time window are available, and are shown respectively at the right and left of the squares. The alternative limits are usually based on short or long double potentials, i.e., the alternative limits are derived from earlier and later slopes in relation to the slope on which the LAT is defined (maximum −dV/dt). They are determined before the algorithm is executed. The principles of the invention disclosed herein are applicable to catheters having other numbers of electrodes.

LAT Optimization.

Figure 3:
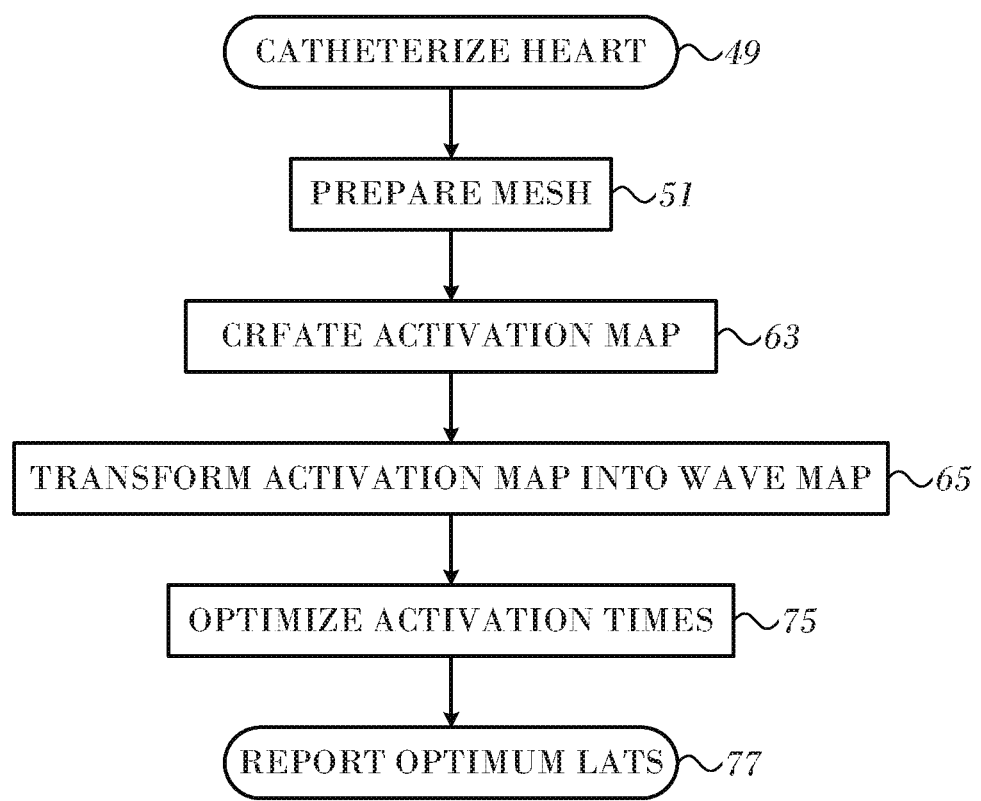
FIG. 3 is a flow diagram of a method for optimizing the LAT for a unipolar electrode in accordance with an embodiment of the invention.

As noted above, LATs in some electrodes can be assigned within the boundaries of a given time window. Alternatively, the LATs can be assigned from alternative slopes in an intracardiac electrogram. The algorithm for the assignment is referred to as a wave propagation coherence function, which, for each electrode, relates a minimum velocity deviation angle ($\alpha_d$) of the propagation vector to the LAT of that electrode. Reference is now made to FIG. 3, which is a high level flow diagram of a method for optimizing the LAT for a unipolar electrode in accordance with an embodiment of the invention. The process steps are shown in a particular linear sequence in FIG. 3 and the other flowcharts herein for clarity of presentation. However, it will be evident that many of them can be performed in parallel, asynchronously, or in different orders. Those skilled in the art will also appreciate that a process could alternatively be represented as a number of interrelated states or events, e.g., in a state diagram. Moreover, not all illustrated process steps may be required to implement the method.

At initial step 49 the heart is catheterized conventionally with a multi-electrode mapping catheter. Catheters such as the PentaRay® NAV or Navistar® Thermocool® catheters, available from Biosense Webster, are suitable for initial step 49. The electrodes of the catheter are placed in galvanic contact with respective locations in one of the atria.

Figure 4:
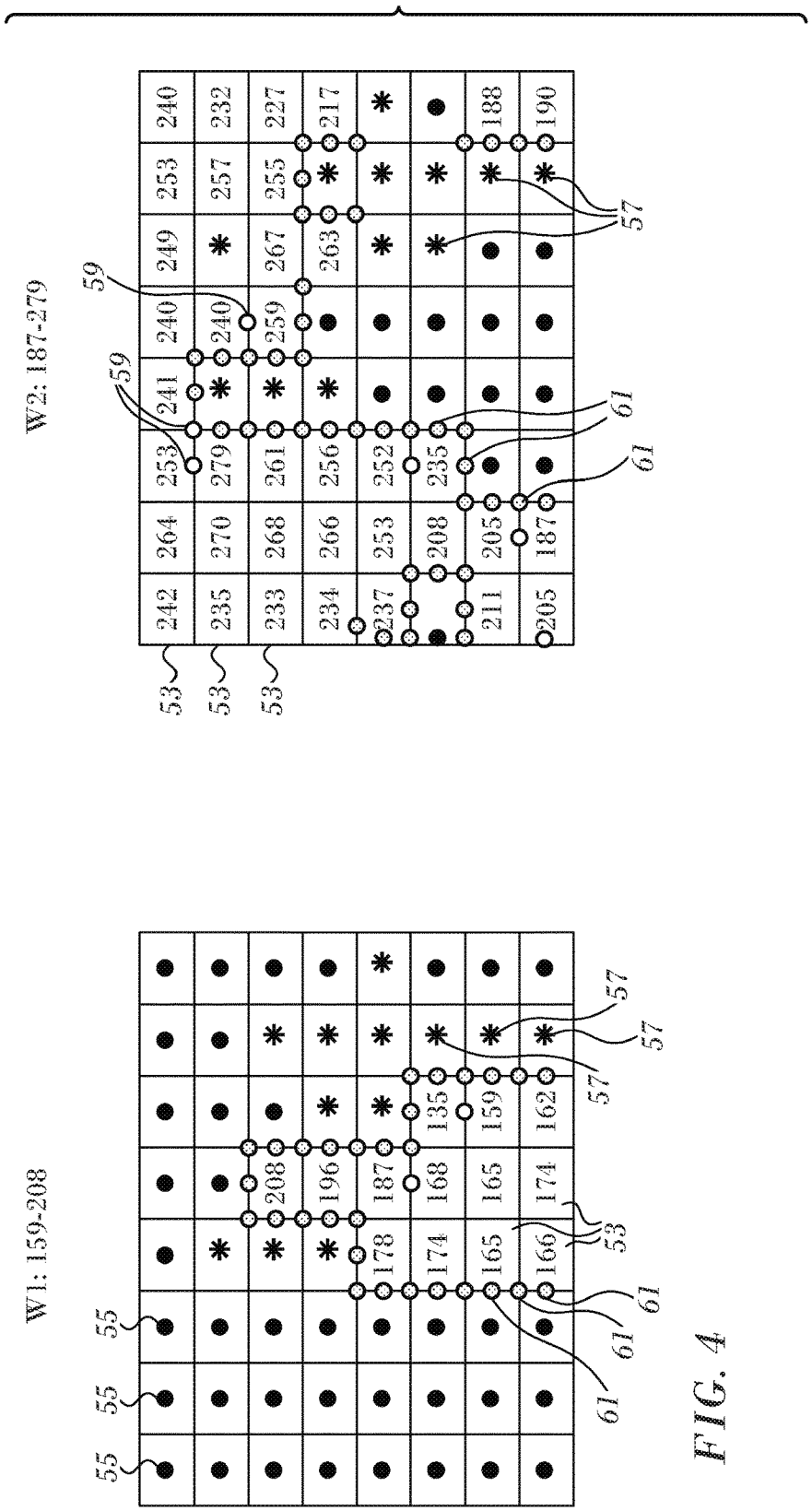
FIG. 4 is a diagram illustrating an electrode grid showing lines of block in atrial fibrillation, in accordance with an embodiment of the invention.

Next, at step 51 The map of electrodes and their locations can be presented as an electrode mesh. The activation map can reveal lines of block. Reference is now made to FIG. 4, which is an exemplary diagram illustrating an electrode grid showing lines of block in atrial fibrillation, in accordance with an embodiment of the invention. Local activation times are indicated in squares 53. Electrode positions 55, some obscured by the squares 53, form a grid. Low quality electrode signals are indicated by asterisks 57. These signals are not reliable for LAT determination. Block points 59 have local activation times that lie outside a time window of interest. Lines of block are indicated by a collection of block points 61.

Next, at step 63 atrial electrical activity is recorded concurrently with the multiple electrodes of the catheter, each having a respective location, which can be determined using the position tracking capabilities of the system 10 (FIG. 1). Atrial depolarization is initially detected, where possible, using conventional methods such as the maximum −dV/dt deflection. Ventricular far-field activity can be excluded using the methods taught in commonly assigned application Ser. No. 14/693,042, which is herein incorporated by reference. The electrograms are segmented into a series frames at respective times.

Next, at step 65 the activation map is transformed into a map of propagation waves. This is accomplished by a process of frame segmentation, which is discussed below. This process may involve modeling the atrium, typically, although not necessarily as a 3-dimensional triangular mesh. Methods for generating the mesh include the Ball-Pivoting Algorithm. Alternatively, the mesh may be generated as a Delaunay triangulation, comprising a plurality of triangles. Frame segmentation in conjunction with the mesh accomplishes the transformation. Frame segmentation is described below in the discussion of FIG. 6.

Figure 5:
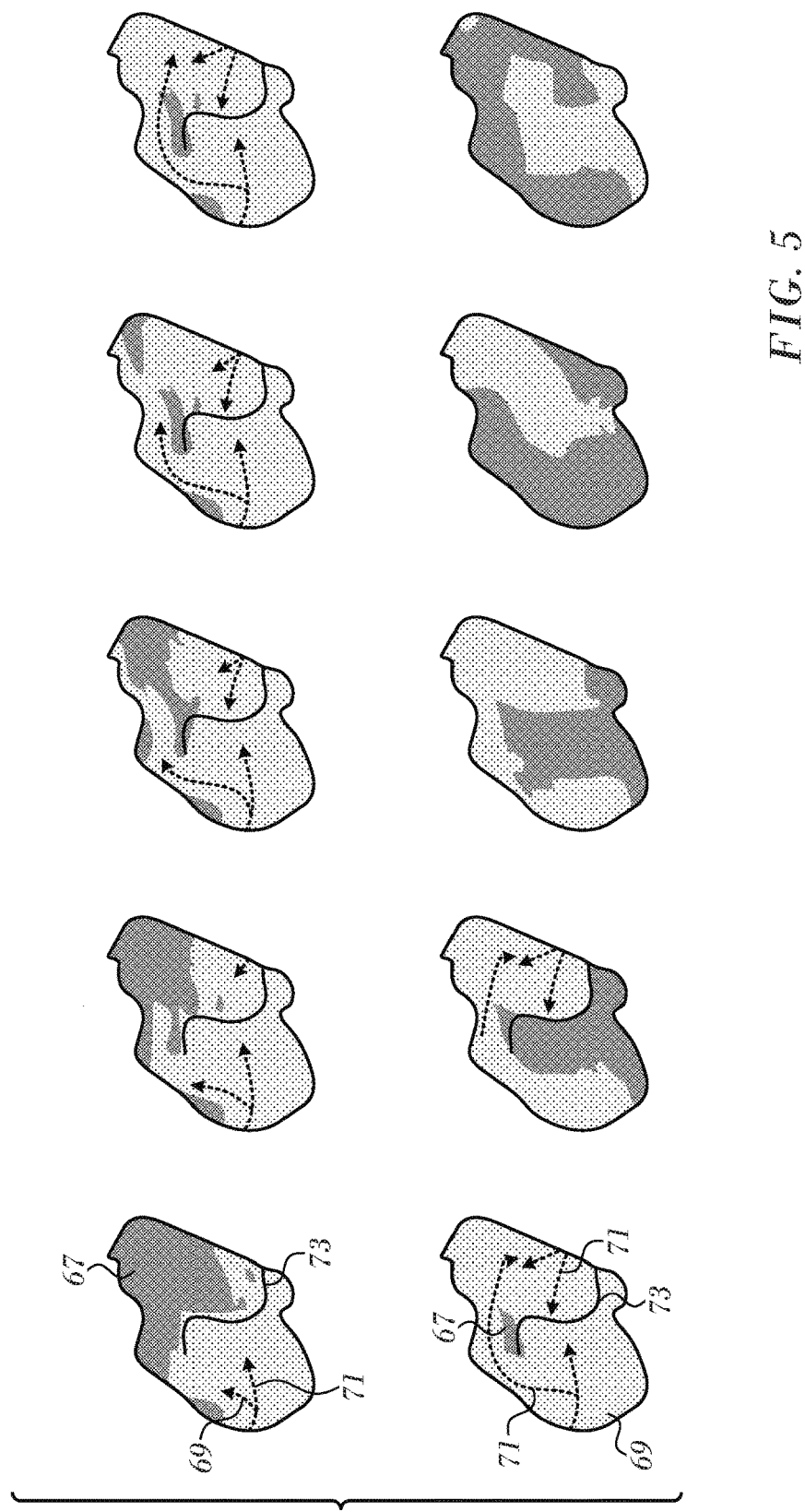
FIG. 5 is a sequence of wave frames in accordance with an embodiment of the invention.

Reference is now made to FIG. 5, which is a sequence of 10 wave frames ranging from 237-399 ms in accordance with an embodiment of the invention. As shown representatively in the two frames at the left of the figure, areas 67 show no active waves. Areas 69 indicate waves 71 separated by lines of block 73. The numbers in the lower left corners of the frames indicate time in ms.

Returning to FIG. 3, at step 75 the activation times of the electrodes are optimized. This is an iterative procedure, which is described in relation to FIG. 15.

Control proceeds to final step 77. For each electrode in which a valid reading was obtained, a fixed LAT or the LAT producing the minimum velocity deviation angle is reported.

Frame Segmentation.

Figure 6:
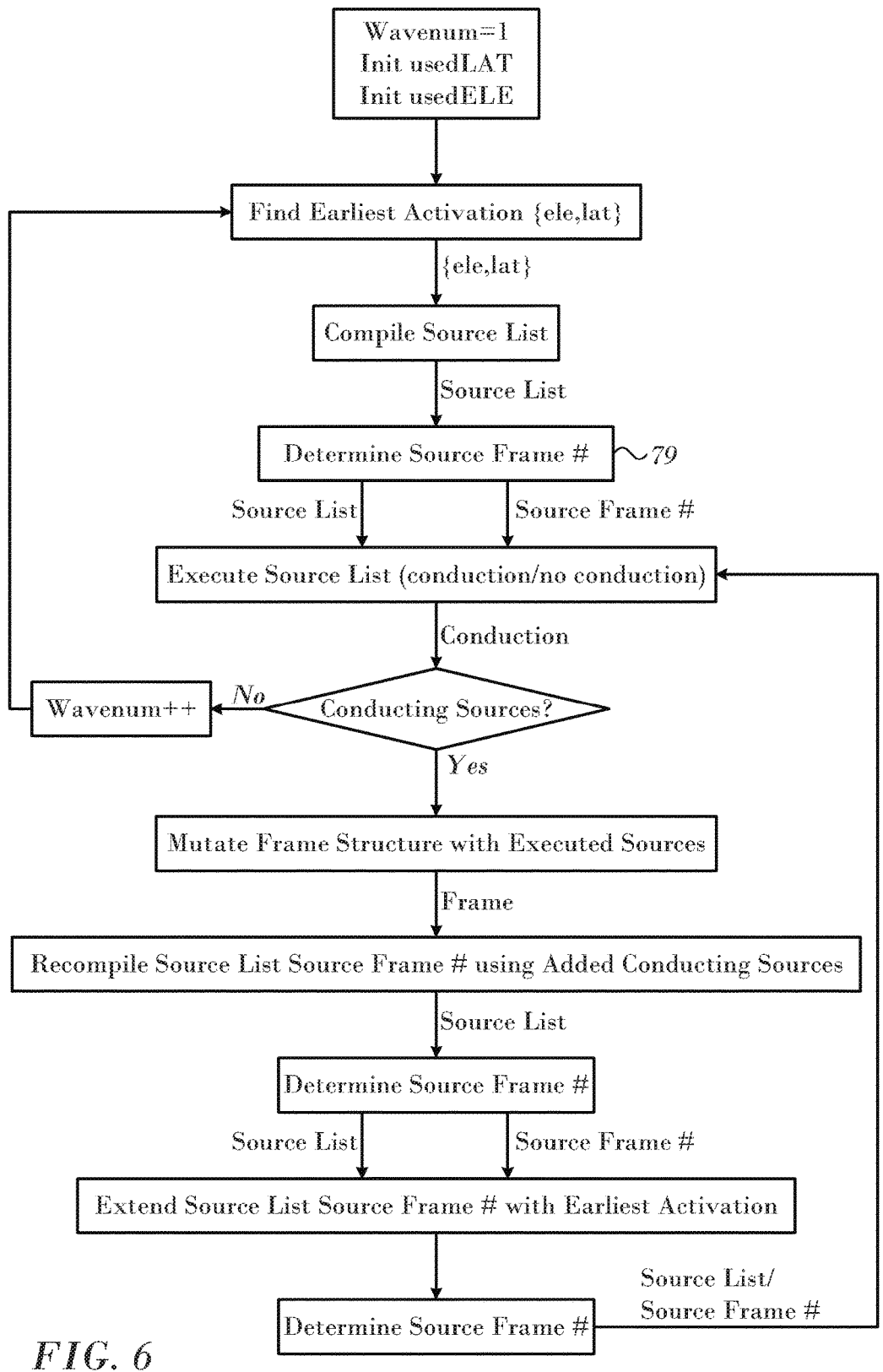
FIG. 6 is a flow diagram illustrating frame segmentation in accordance with an embodiment of the invention.

Reference is now made to FIG. 6, which is a flow diagram illustrating frame segmentation as noted in step 65 (FIG. 3). The diagram describes frame segmentation in accordance with an embodiment of the invention. Frames are filled with LATs that most logically relate to each other. Within this process, conduction velocity is calculated. Conduction blocks are determined by reference to corresponding LATs in subsequent frames.

A source list is maintained during the course of execution of the algorithm. The source list contains electrode numbers and associated LATs to be checked against neighboring LATs for block or conduction. Electrode numbers that are found to be conductive are added to the source list and checked in the next run of the algorithm. In this way, the algorithm grows a region of electrode numbers that belong to the same wave.

A source frame is determined in block 79. The input to this block is the frame structure, a distance matrix and the LAT obtained from the source electrode. The output of block 79 is the frame number for the source electrode. Assignment of a frame number is based on vacancy of frames at the LAT of the source electrode. For all vacant frames the following characteristics are calculated in order to support an assignment decision, using Matlab routines as shown in Table 2.

TABLE 2

| Characteristic | Matlab Vector (Unit) |
| --- | --- |
| Determine vector of vacant frame(s)<br>1 = Frame is vacant at source electrode position<br>2 = Frame is already occupied at electrode position | vacantframes(1) |
| Calculate closest LAT vs. source electrode/LAT<br>1. Minimum \|dLAT\|between existing electrode/LAT and source LAT | closestLAT(ms) |
| Determine adjacency to already existing neighboring electrodes.<br>1 = solitary electrode, no neighbors<br>0 = neighbors around electrode available in frame(s) | solonele(0, 1) |
| Conduction or block situation<br>1 = Conduction to any of the neighboring electrodes<br>0 = No conduction to any of the neighboring electrode or when no neighboring electrodes available (i.e., when solonele = 1) | condnele(0, 1) |
| Maximum CV between source electrode neighboring electrodes<br>Number = Maximum CV between source electrode and one<br>NaN = When no neighboring electrodes are available | Maxcvnele (num, NaN) |

Based on the characteristics for each vacant frame the decision rules are given in pseudocode in Listing 1.

Listing 1

```
If no vacant frames are availableactMinMap
    Source {ele/LAT} is assigned to the next frame
elseif frames are available with one or more conducting first order
neighbor activation(s)
    Source {ele/LAT} is assigned to the frame with closest LAT
elseif no frames with conducting neighboring activation are available
    if closest LAT<100 ms(AF cycle)
        Source {ele/LAT} is assigned to the frame with closest LAT
    else
        Source {ele/LAT} is assigned to the next frame
    end
end.
```

Figure 7:
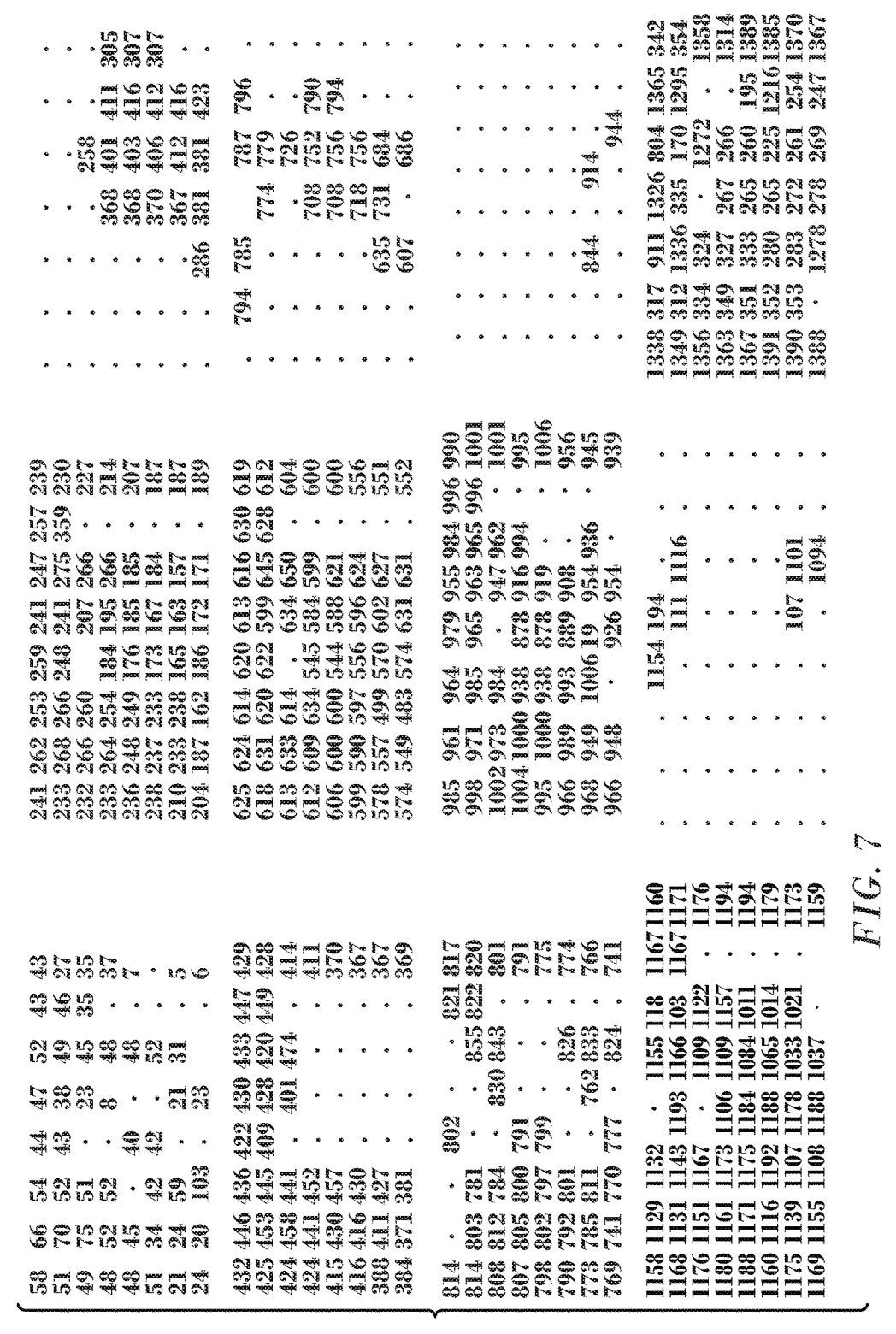

Reference is now made to FIG. 7, which is an exemplary frame segmentation map produced by the above-noted algorithm using Matlab routines, in accordance with an embodiment of the invention. Blank areas in the frames can be attributed to missing electrodes, or to a wave that resides in the next frame as a result of reassignment of values when there is an inter-wave block detected during the frame segmentation process.

Figure 8:
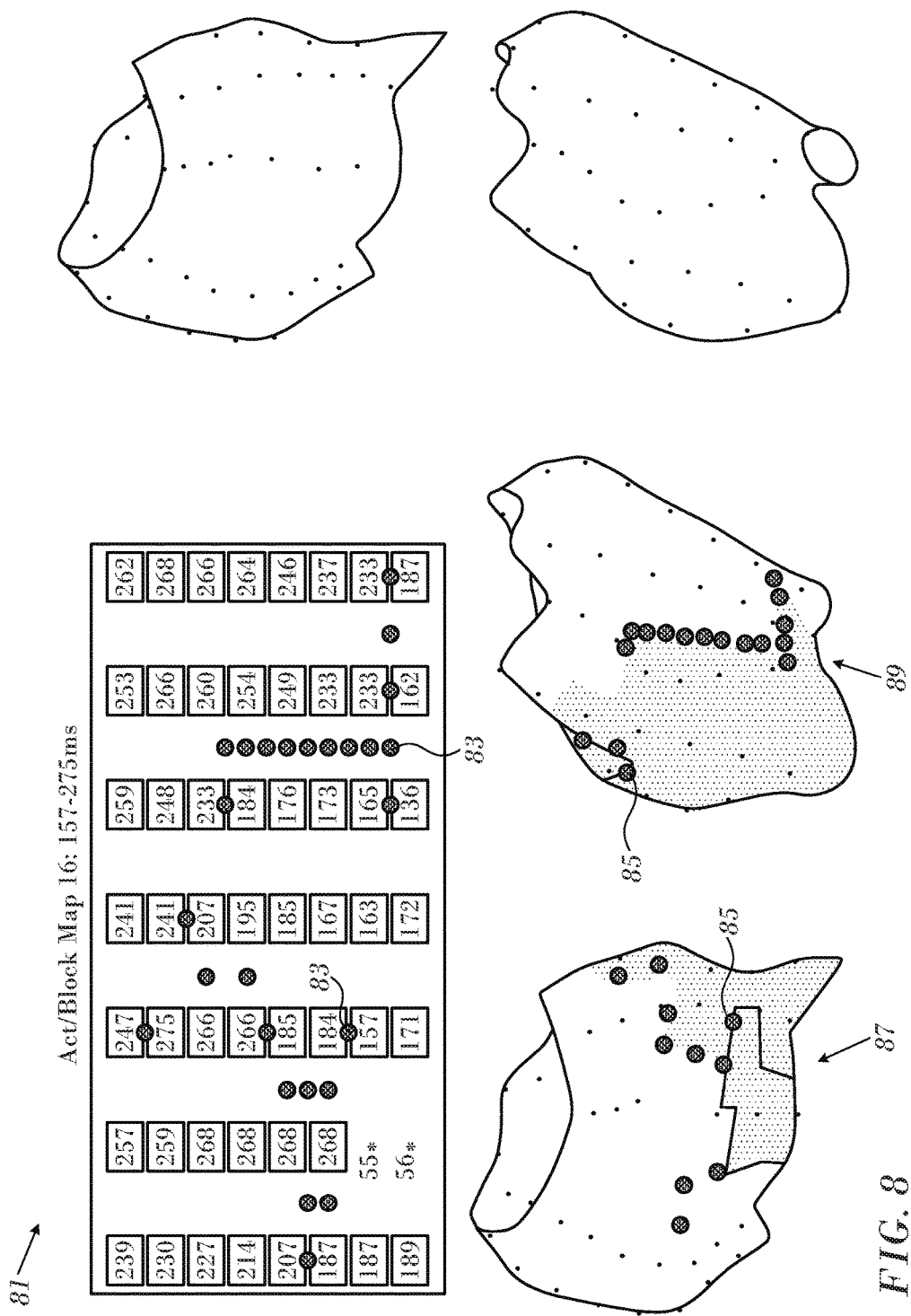
FIG. 8 is a composite diagram showing a frame segmentation matrix and electroanatomic maps in accordance with an embodiment of the invention.

Reference is now made to FIG. 8, which is a composite diagram showing an exemplary frame segmentation matrix 81 and electroanatomic maps produced by the above-noted algorithm and Matlab routines, in accordance with an embodiment of the invention. Lines of block are indicated by dots, e.g., dots 83 on the matrix 81 and dots 85 on maps 87, 89.

Region Growing.

Figure 9:
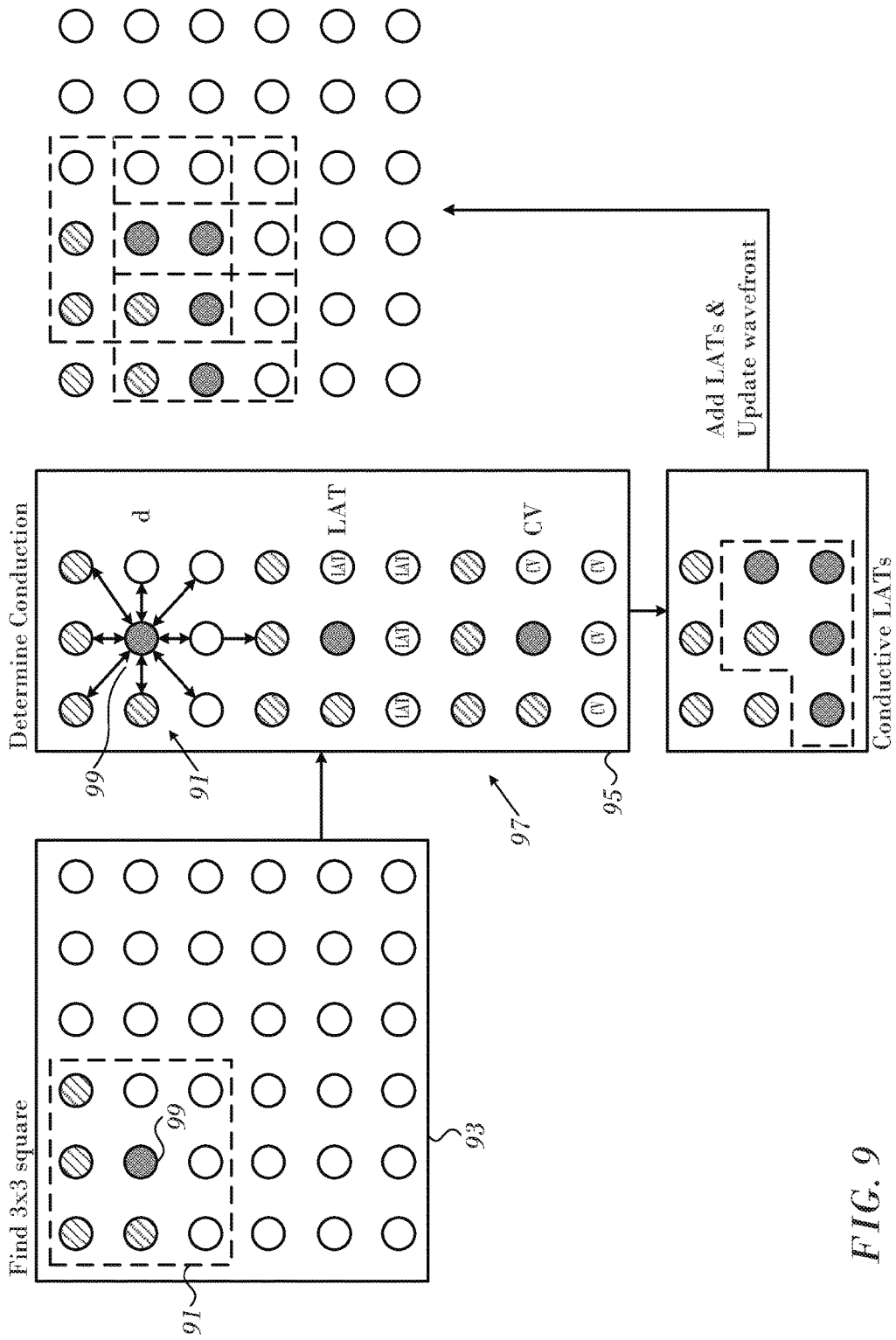
FIG. 9 is a diagram illustrating region growing in accordance with an embodiment of the invention.

Detection of atrial fibrillation waves by an electrode mesh involve a region growing algorithm and a frame generation and segmentation algorithm. Reference is now made to FIG. 9, which is a diagram explaining a process of region growing, in accordance with an embodiment of the invention. The process is iterative. It is convenient to identify neighboring electrodes around the center of a 3×3 grid, e.g., by identification numbers. For purposes of region growing a normalized conduction velocity is calculated, using the LATs of the center electrode and the eight neighboring electrodes in the 3×3 grid.

A 3×3 square grid 91 of electrodes is identified in block 93, shown as a square delineated by a broken line.

Next, in block 95 conduction is evaluated in the square grid 91 at stage 97. This process requires:

(1) calculating the 3-dimensional distance between center electrode 99 and neighboring electrodes in the square grid 91;

(2) determining the local activation time interval between the center electrode 99 and the neighboring electrodes, Additional information is available for extension of the region:

(1) LAT time windows. These provide indications of LAT inaccuracy.
(2) Conduction velocity vector of four 2×2 squares within the 3×3 grid.
(3) A primary annotation and FF slope (secondary annotation) for neighboring IC-ECG.
(4) Quality of the IC-ECG and the LAT quality.

Conduction integrity or a conduction block may now be determined based on $$CV_{norm} = d(LAT)/d(LOC),$$ where $LOC$ refers to the location of an intracardiac electrode $$CV_{norm} \geq CV.$$

A block is indicated when $CV_{norm} \leq CV_{norm\_min}$, in which case:

$$CV \leq CV_{norm\_min}.$$

An alternative conduction detection strategy includes determining the magnitude of conduction velocity vector only for high quality IC-ECGs and LATs. This method suffers from sensitivity to LAT inaccuracies.

Another alternative conduction detection strategy involves fitting a 3×3 fit of a bi-quadratic surface on LATs using standard methods. This results in an over-determined solution, but is more robust against LAT inaccuracies.

Further details regarding frame segmentation and region growing are found in the above-noted U.S. Patent Publication No. 2016/0045123.

Mapping of Atrial Activation.

Figure 10:
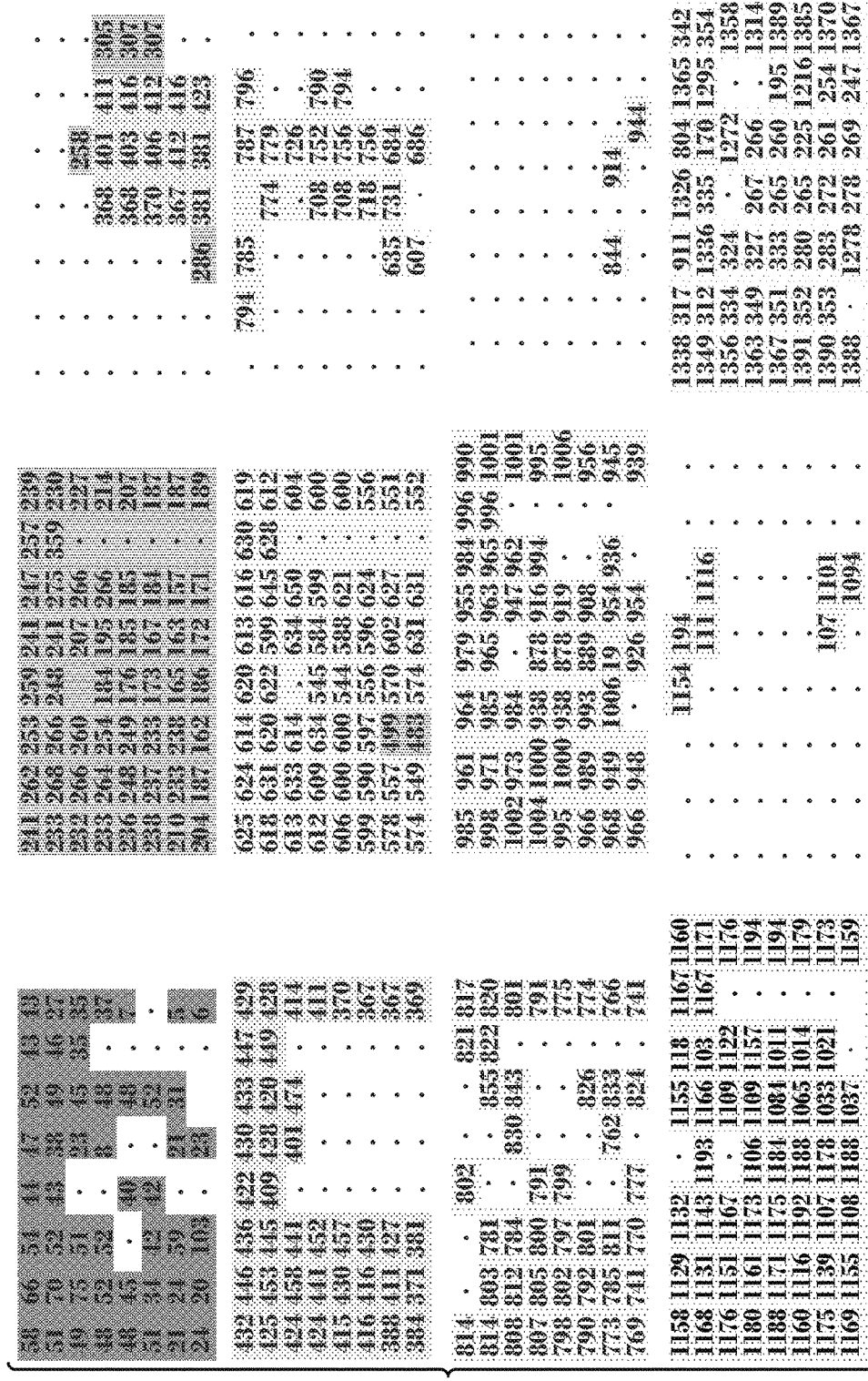
FIG. 10 is a portion of a segmentation map, which was produced in accordance with an embodiment of the invention.

Reference is now made to FIG. 10, which is a portion of a typical frame segmentation map, which was produced using the procedure described above in accordance with an embodiment of the invention. A single frame may include more than one wave, and a given wave can extend over multiple frames. In such cases waves can be differentiated from one another by line hatching patterns.

Interpolation is employed in embodiments of the invention to produce activation waves on a more refined catheter mesh, as noted above. Advantages of interpolation include better spatiotemporally defined activation times when there is a relatively large signal amplitude and negative slope. When this is not the case, possible alternative (earlier or later) activation times are revealed. These are characterized by large negative slope near the LAT.

Because the electrode mesh is relatively coarse-grained for purposes of display, 3-dimensional mapping systems, such as the above-noted CARTO 3 System have interpolated sample points by using a weighted mean that is configured to be inversely proportional to the geodesic distance between points on the surface and have displayed the results in pseudo-colored maps.

Other interpolation techniques include Laplacian interpolation. However, it should be noted that conventional surface Laplacian interpolation may not provide a smooth LAT/wave pattern due to irregularities in the anatomical meshes, e.g., variations in distances between vertices. These problems can be mitigated by application of the teachings of commonly assigned application Ser. No. 15/009,285 entitled *High Definition Coloring of Heart Chambers*, which is herein incorporated by reference.

Interpolation techniques employed in embodiments of the invention facilitate treatment of cases in which the signal lacks an abrupt amplitude jump as a "fuzzy LAT". These are described below.

Figure 11:
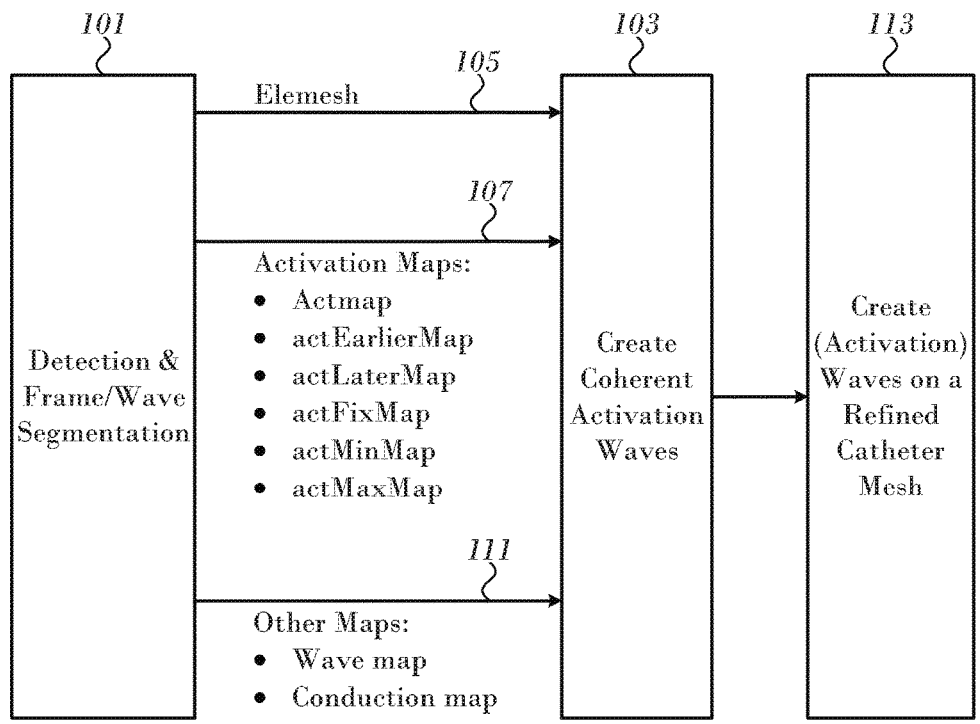
FIG. 11 is a block diagram illustrating activation wave representation in accordance with an embodiment of the invention.

Reference is now made to FIG. 11, which is a block diagram illustrating activation wave representation in accordance with an embodiment of the invention.

In block 101 concurrent acquisition of intracardiac electrograms and frame segmentation occur, as described above.

Block 103 generates activation waves at the resolution of the electrode mesh. Block 103 receives the electrograms from the electrode mesh an output of block 101 as signals 105 (ELEMESH). The following activation maps are produced in block 101, and output as signal 107:

actMap The most likely LAT per electrode,
actFixMap If slope and amplitude >threshold, LAT is fixed,
actInvalid No valid LAT available for this electrode.

Additionally, the following activations maps may be available for electrodes in which the LAT is not fixed, but may be varied according to the algorithms disclosed herein:
actEarlierMap Alternative earlier LAT,
actLaterMap Alternative later LAT,
actMinMap LAT lower limit,
actMaxMap LAT upper limit.

Additional wave maps and conduction velocity (CV) maps are output from block 101 as signal 111.

Block 113 transforms the wave maps produced in block 103 into a higher resolution format, typically using a more detailed mesh and the procedures described above. Interpolation procedures executed in block 113 produce coherent activation waves, which can involve adaptation of a range of activation times, or earlier or later activation times when a well-defined LAT is not available.

Map Interpolation.

Figure 12:
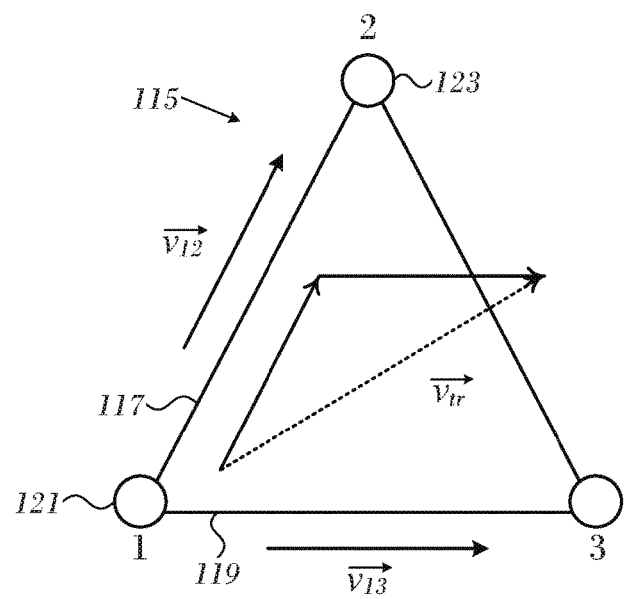
FIG. 12 is a diagram illustrating the calculation of velocity vectors for an electrical wave on a mesh in accordance with an embodiment of the invention.

As noted above, creation of coherent wave involves map interpolation. The procedure is described with respect to a triangular mesh is assumed. Other mesh configurations can be decomposed into triangles. Reference is now made to FIG. 12, which is a diagram illustrating the calculation of velocity vectors for an electrical wave on a mesh in accordance with an embodiment of the invention. Triangle 115 has edges, including edges 117, 119. A velocity vector exists at each edge. For example, the velocity vector $\vec{v}_{12}$ for edge 117 is given by $$\vec{v}_{12} = \frac{d_{12}}{(lat_2 - lat_1)} \qquad \text{Eq. (1)}$$

where $d_{12}$ is the distance between vertices 121, 123 of triangle 115, and $lat_1$ and $lat_2$ are the activation times at vertices 121, 123. The velocity vector for edge 119 is calculated in like manner.

The velocity $\vec{v}_{tr}$ through triangle 115 is the sum of velocities along edges 117, 119:

$$\vec{v}_{tr} = \vec{v}_{12} + \vec{v}_{13} \qquad \text{Eq. (2).}$$

Figure 13:
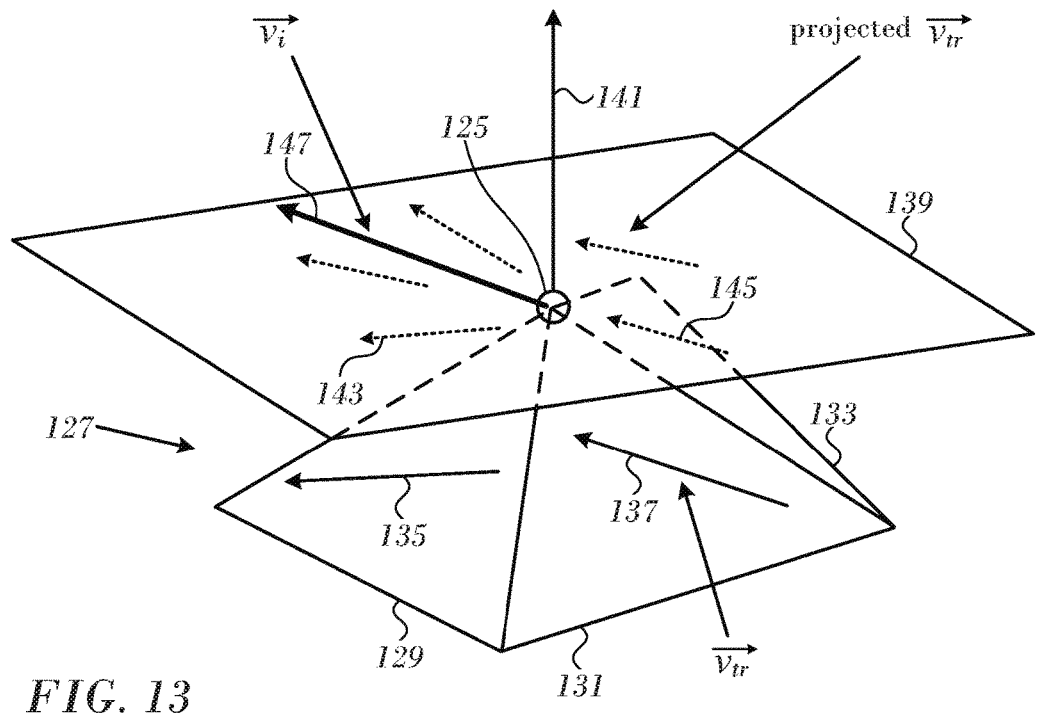
FIG. 13 is a diagram illustrating the calculation of vector velocity at a vertex of a triangular mesh in accordance with an embodiment of the invention.

Reference is now made to FIG. 13, which illustrates the calculation of the vector velocity at a vertex 125 of a portion of a triangular mesh 127 in accordance with an embodiment of the invention. The vertex 125 is formed by connected triangles 129, 131, 133 having respective velocity vectors that are calculated according to the equations in FIG. 12. Velocity vectors 135, 137 of triangles 129, 131 are shown. The velocity vectors of all triangles connected to vertex 125, including the velocity vectors 135, 137, are projected onto a plane 139 that is defined by a normal 141 to the vertex 125. For example, vectors 143, 145 are the projections of velocity vectors 135, 137 ($\vec{v}_{tr}$) on the plane 139, respectively. Velocity vector 147 ($\vec{v}_1$) is the average of all the projected velocity vectors of the triangles connected to vertex 125.

Figure 14:
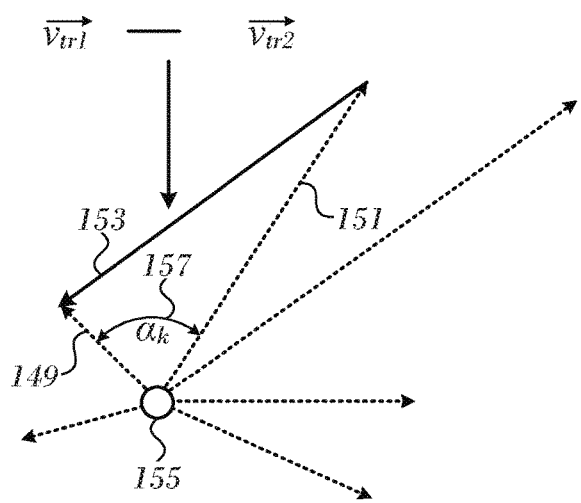
FIG. 14 is a diagram illustrating the calculation of certain variables useful in wave mapping in accordance with an embodiment of the invention.

Reference is now made to FIG. 14, which is a diagram illustrating the calculation of certain variables useful in wave mapping in accordance with an embodiment of the invention. Projected velocity vectors, including vectors 149, 151 and their difference vector 153 are positioned in relation to a vertex 155. Angle 157 between two projected velocity vectors, e.g., the vectors 149, 151, is denoted by $\alpha_k$.

The velocity deviation vector $v_d$ at a vertex is given by the formula $$v_d = \sum_{tr1=1}^{n} \sum_{tr2=tr1+1}^{n} \|\vec{v}_{tr1} - \vec{v}_{tr2}\| \qquad \text{Eq. (3)}$$

where tr1 and tr2 are connected triangles (not shown) at the vertex, and $\vec{v}_{tr1}$, $\vec{v}_{tr2}$ are their velocity vectors. According to embodiments of the invention, the velocity deviation vector is minimized in order to extract propagation waves from the intracardiac electrograms. In another application, when it is desired to define non-propagating waves, i.e., blocked waves, the velocity deviation vector may be maximized. In general a block is assumed when conduction velocity is below a minimum, typically 0.2 M/s.

Continuing to refer to FIG. 14, the velocity deviation angle ($\overline{\alpha_d}$) at the vertex 155 is given by $$\overline{\alpha_d} = \frac{1}{n}\sum_{k=1}^{n} \alpha_k \qquad \text{Eq. (4)}$$

where n is the number of connecting triangles forming the common vertex 155. In general waves are coherent when the velocity deviation angle is small. In order to obtain propagation waves the velocity deviation angle is minimized.

Coherent Mapping Algorithm.

Reverting to FIG. 11, it is assumed that maps included in the signals 107, 111 are available and that the electrodes have been represented as a triangular mesh.

Figure 15:
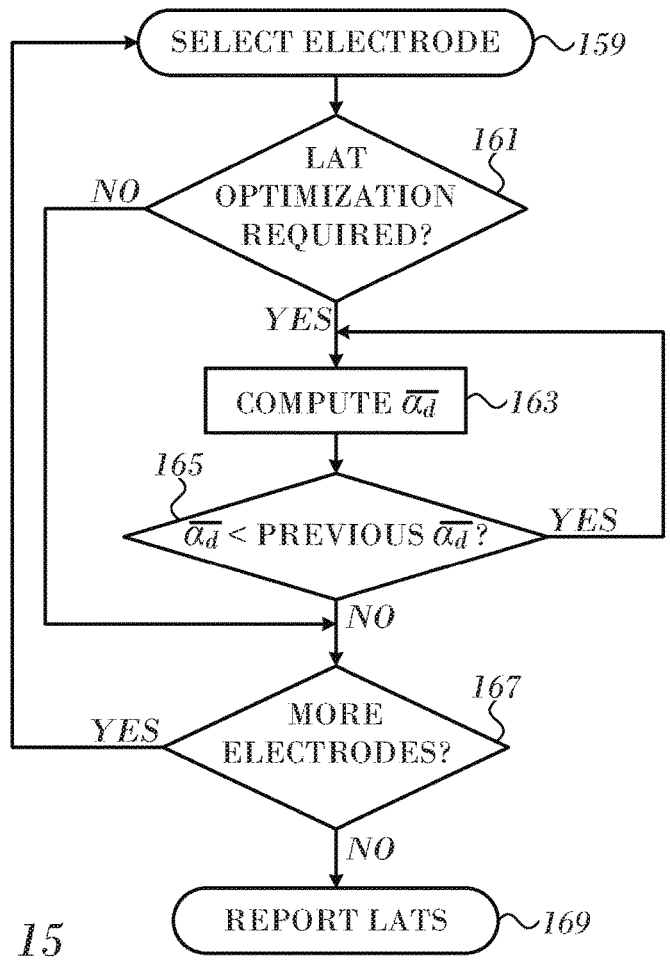
FIG. 15 is a flow chart of a method for mapping coherent propagation waves in the heart in accordance with an embodiment of the invention.

The following procedure is a detailed flow chart of one embodiment of step 75 (FIG. 3), which may be performed in block 103. Reference is now made to FIG. 15, which is a flow chart of a method for mapping coherent propagation waves in the heart in accordance with an embodiment of the invention. At initial step 159 information, including the LAT, obtained from one of the electrodes of the catheter is selected.

Next, at decision step 161, it is determined if the LAT obtained from the current electrode needs to be optimized. If the determination at decision step 161 is negative, i.e., the reading is invalid, or the LAT was calculated from a well-defined negative slope (maximum –dV/dt), and is therefore fixed, then no further action need be taken. Control proceeds directly to decision step 167, which is described below.

If the determination at decision step 161 is affirmative, then control proceeds to step 163, where the velocity deviation angle ($\overline{\alpha_d}$) is minimized for the vertex on the mesh that corresponds to the current electrode. The optimization is accomplished by adjusting the LATs used to compute the velocity vectors for the connecting triangles (Equation 1). The adjustment limits for the current electrode are obtained from the above-noted maps actMinMap and actMaxMap.

Next, at decision step 165 it is determined if the velocity deviation angle that was computed in the current iteration of step 163 has changed from the value computed in the previous iteration by more than a predetermined tolerance. If the determination is affirmative, then the algorithm is continuing to progress. Control returns to step 163 to iterate the loop.

If the determination at decision step 165 is negative, then it is determined that the value of the velocity deviation angle has converged, and there is no need to continue iterating step 163. Control proceeds to decision step 167, where it is determined if data from more electrodes remain to be processed. If the determination is affirmative, then control proceeds returns to initial step 159 and another electrode is chosen.

If the determination at decision step 167 is negative, then control proceeds to final step 169. The optimized LATs are reported.

First Alternate Embodiment.

In this embodiment, alternative activation times before and/or after the LAT slope are identified accommodating short and long double potentials. These alternate LATs can be involved in the optimization of the minimum velocity deviation angle.

Figure 16:
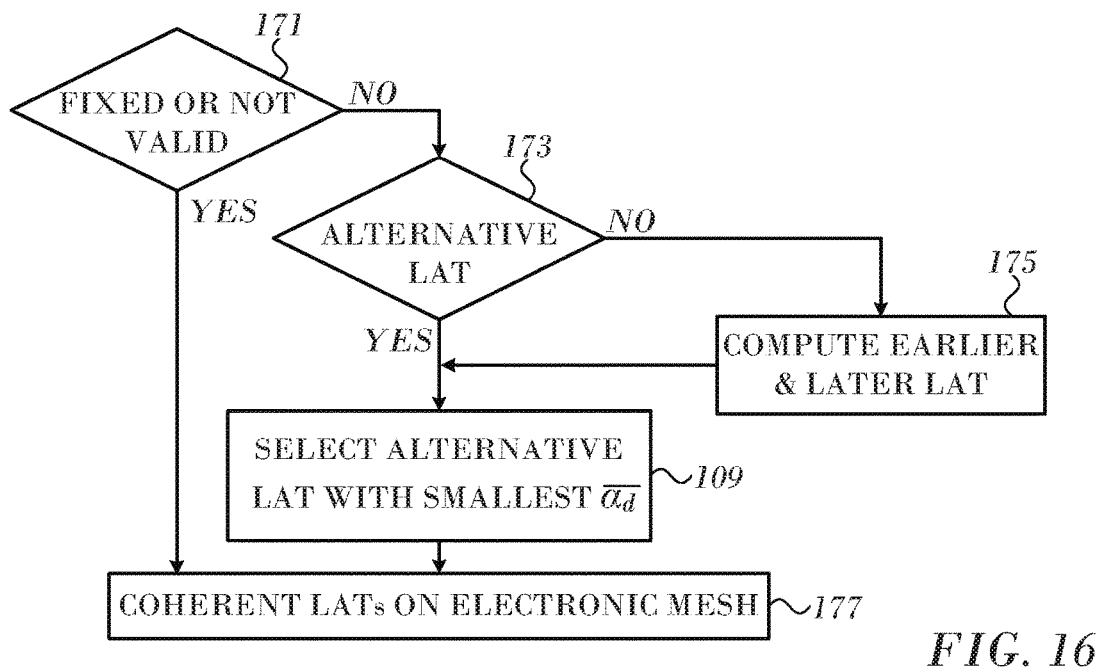
FIG. 16 is a flow chart of a method for mapping coherent propagation waves in the heart in accordance with an alternate embodiment of the invention.

Reference is now made to FIG. 16, which is a flow chart of a method for mapping coherent propagation waves in the heart in accordance with an alternate embodiment of the invention in which alternative activation times are sought. The procedures in this embodiment are repeated for each electrode. The procedures shown in FIG. 16 may be coordinated with the method described with respect to FIG. 15, for example, when the iterative loop comprising step 163 and decision step 165 fails to converge or otherwise fails to result in a reliable optimization of the LAT for a particular electrode. Such cases arise when the signals are of low amplitude or low quality, or are interfered with by far field potentials that cannot be completely removed.

At decision step 171 it is determined if the LAT for a particular electrode is fixed or the reading is invalid. If the determination at decision step 171 is affirmative, then the remainder of the algorithm is omitted, and control proceeds directly to final step 177.

In some embodiments, in order to spare computer resources, the functional maps related to alternative LATs (actEarlierMap, actLaterMap) are not automatically generated and alternative activations may not yet be available. If the determination at decision step 171 is negative, then at decision step 173, it is determined if an alternative LAT for the current electrode already exists.

If the determination at decision step 173 is affirmative, then control proceeds to optimization step 109, in which the iterative loop described above in step 163 and decision step 165 is executed, using the alternative LAT that corresponds to the smallest velocity deviation angle among the alternative possibilities. When both earlier and later LATs are available, the optimization is performed for both of them, and the optimized LAT is selected from the result that corresponds to the smaller value of the velocity deviation angle.

If the determination at decision step 173 is negative, then earlier and later alternative LATs are computed in step 175. These are determined from secondary slopes found within a window of ±40 ms about a primary slope. Thereafter, optimization step 109 is performed based on the computed alternative LATs as described above.

After performing optimization step 109 in final step 177 coherent LATs for the electrode mesh are reported.

Figure 17:
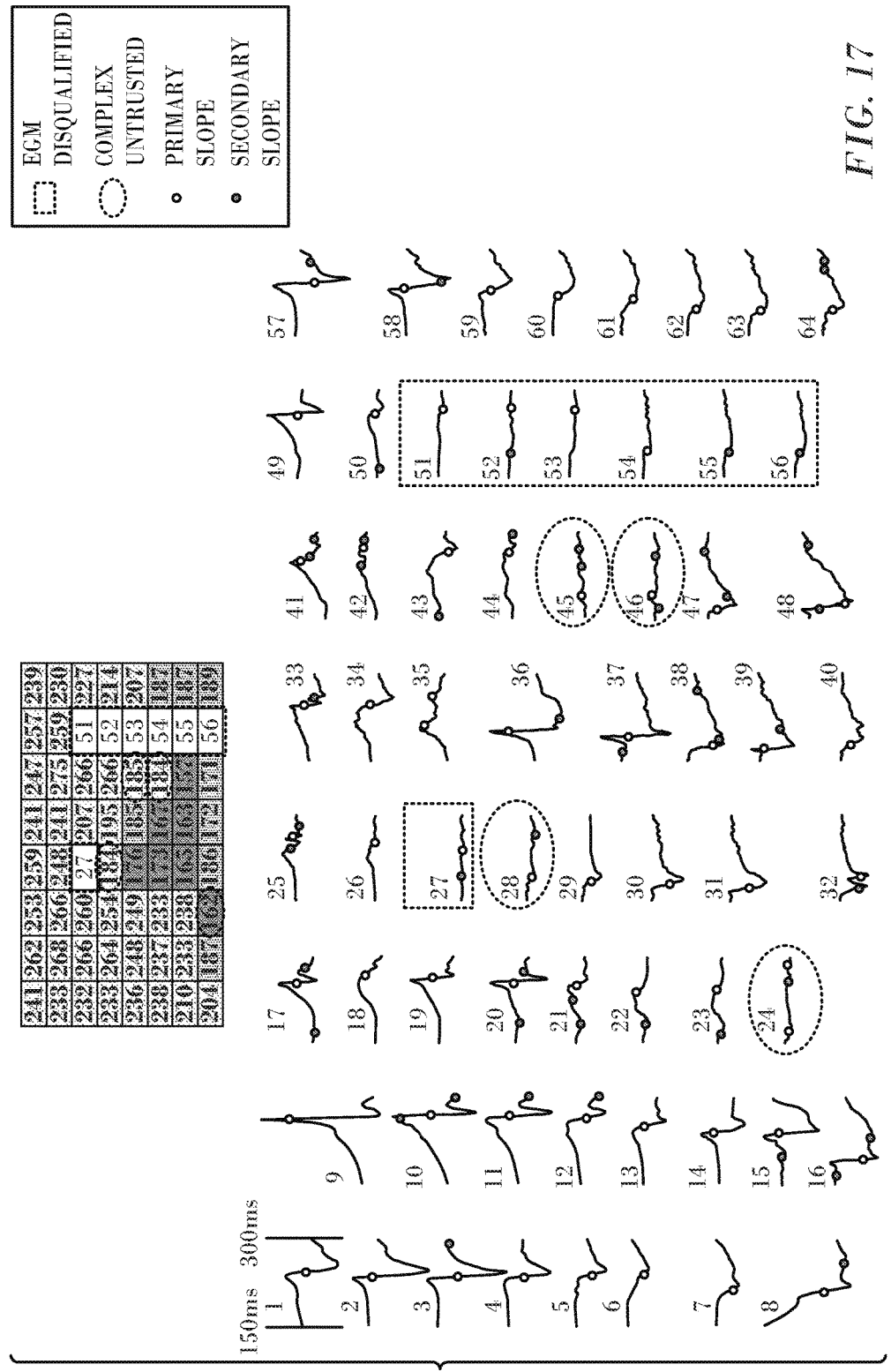
FIG. 17 is an activation map of data that can be used in the method described with respect to FIG. 16 in accordance with an embodiment of the invention.

Reference is now made to FIG. 17, which is an exemplary activation map of data that can be used in the method described with respect to FIG. 16 in accordance with an embodiment of the invention. The activation times for the electrode mesh are shown in the upper left of the figure. Voltage tracings of the electrodes are presented, with indications for typical primary and secondary slopes. Indicators for lack of reliability and disqualification indications are shown respectively as ovals and squares surrounding the tracings.

Interpolation to Refined Mesh and Anatomical Map.

Figure 18:
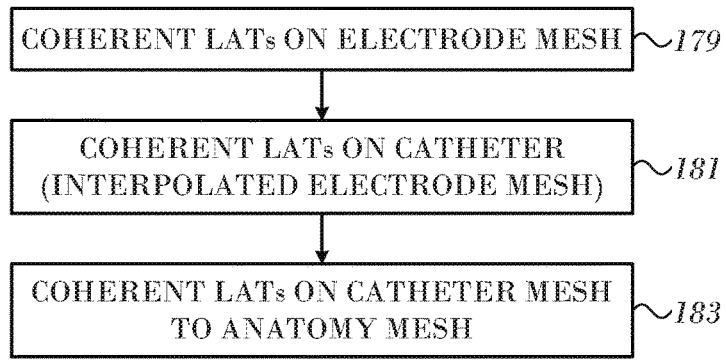
FIG. 18 is a flow chart for relating LATs of an electrode mesh to cardiac anatomy on a more refined mesh in accordance with an embodiment of the invention.

The procedures described above produce coherent LATs on a relatively coarse electrode mesh. Reference is now made to FIG. 18, which is a flow chart for relating LATs of an electrode mesh to cardiac anatomy represented on a more refined triangular mesh in accordance with an embodiment of the invention. At initial step 179, coherent LATs are produced for an electrode mesh, using the LAT optimization procedures described above.

Next, at step 181, in order to produce a map with higher resolution, the coherent LATs on the electrode mesh are interpolated using a bilinear interpolation algorithm for each square of 2×2 electrodes, taking into account inter- and intra-wave blocks, which can be identified using the teachings of the above-noted U.S. Patent Publication No. 2016/0045123. This step results in a relatively fine-grained interpolated mesh Then, in final step 183, the interpolated mesh is mapped to cardiac anatomical landmarks. The positions of the electrodes are mapped to an anatomical model, e.g., an anatomical mesh only when the distance between the electrode position and an anatomical mesh point is less than 20 mm. Current position sensing equipment, such as the above-noted CARTO system, can determine the 3-dimensional position of the catheter electrodes within 1-2 mm. However, the mapping can result in either oversampling or undersampling (on average) of anatomical mesh points. Oversampling occurs when the number of catheter electrode mesh points exceeds the number of close anatomical mesh points (<20 mm separation). Undersampling occurs if the number of close anatomical mesh points exceeds the number of catheter electrode mesh points. Once all the catheter electrode mesh points that are close to an anatomical mesh point have been mapped, the remaining catheter electrode mesh points are marked as invalid. Interpolation of unallocated anatomical mesh points (<20 mm) should preferably be interpolated because the anatomical mesh is undersampled relative to the electrode mesh (n=64).

Catheters can deform the heart, so that an anatomical model would not be exact if it were prepared off-line, rather than during the session. The distortion varies with catheter models. It is recommended to repeatedly identify and locate catheter electrodes that are close to or in contact with the endocardial surface, based on slope analysis of the intracardiac electrogram, and to compensate for the distortion by adjusting the anatomical mesh as necessary during the session. In this way, the propagation waves can be accurately correlated with the cardiac anatomy throughout the session.

Figure 19:
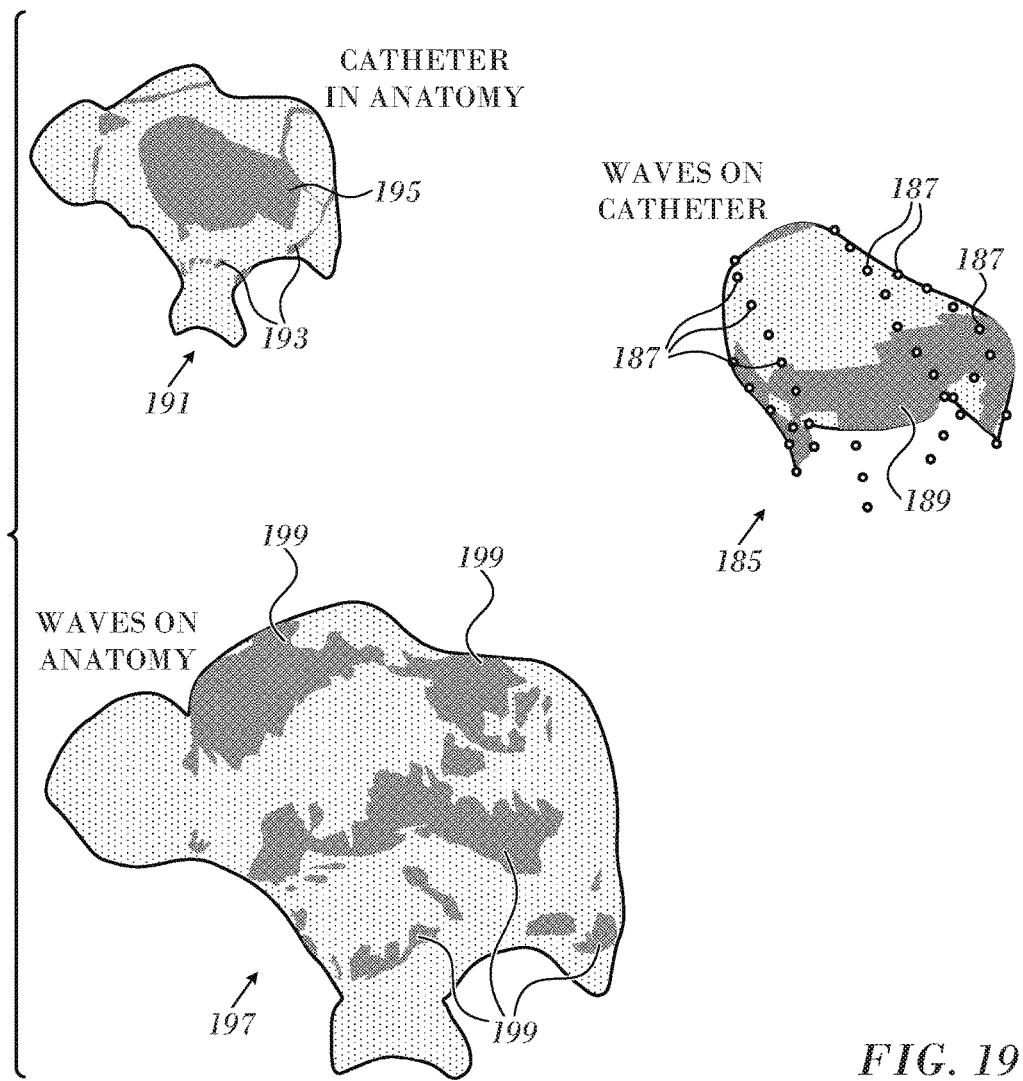
FIG. 19 is a group of diagrams illustrating stages in the method of FIG. 18 in accordance with an embodiment of the invention.

Reference is now made to FIG. 19, which is a group of diagrams illustrating stages in the method of FIG. 18 in accordance with an embodiment of the invention. Diagram 185 at the right of the figure represents a smoothed map of numbered catheter electrode mesh points 187 (some of the point identifiers are omitted for clarity). The map shows a propagation wave 189 in the lower portion of the diagram 185.

Diagram 191 shows the catheter electrodes fitted to an anatomical model of an atrium. The distribution of the catheter electrodes is shown on the model as irregular linear markings 193. A central area 195 represents the envelope of the mapping catheter that may or may not be in contact with the endocardial surface.

Diagram 197 is a map representing the positions of the catheter electrode mesh points mapped to the anatomical model, which, as noted above, is a fine-grained triangular mesh. Several propagation waves 199 are shown.

Second Alternate Embodiment.

The LAT adjustment within a range described in the previous embodiment is a special case of a broader technique for designating an activation time, which is referred to herein as a "fuzzy activation time" or "fuzzy LAT". Fuzzy LATs refer to fuzzy numbers according to the general theories of fuzzy logic, fuzzy math rules, and fuzzy sets described originally by Lofti Zadeh and later by Bart Kosko, et al. In this concept variables are assigned truth values, which may be any real number between 0 and 1. By contrast, in Boolean logic, the truth values of variables are 0 or 1 exclusively. In this embodiment a truth value is assigned to LATs that reduces when deviating from the detected LAT. Moreover, fuzzy LATs can be combined using fuzzy math rules. Coherent maps produced using fuzzy LATs are referred to as "fuzzy coherent maps". This concept has been reduced to a range of LATs, possibility including earlier and later alternative LATs to create coherent maps.

Notation for Electrode Mesh.

In a mapping array, ne is the number of electrodes in the array:

$LAT_e$ is the LAT (ms) at electrode e, $1 \le e \le ne$, $\mu_e$ is a fuzzy membership function for the activation at electrode e. For the surface of a mesh, $\mu_e=1$. The fuzzy membership function defines the fuzzy LAT. The LAT associated with the maximum $-dV/dt$ is assigned a value of 1. The triangular shaped membership function tapers off to zero at the peak (earlier) and valley (later) associated with the negative slope and the LAT. The area under the membership function is normalized to 1, Therefore, relatively steep negative slopes provide sharp high amplitude membership functions with a narrow base equal to the time between the peak and valley demarcating the negative slope. In contrast, shallow negative slopes provide broad-based low amplitude membership functions.

For a set of local activation times mapped on an anatomical mesh:

nu is the number of vertices in the mesh.

$LAT_u$ is the LAT at a mesh vertex u (ms), $1 \le u \le nu$.

Figure 25:
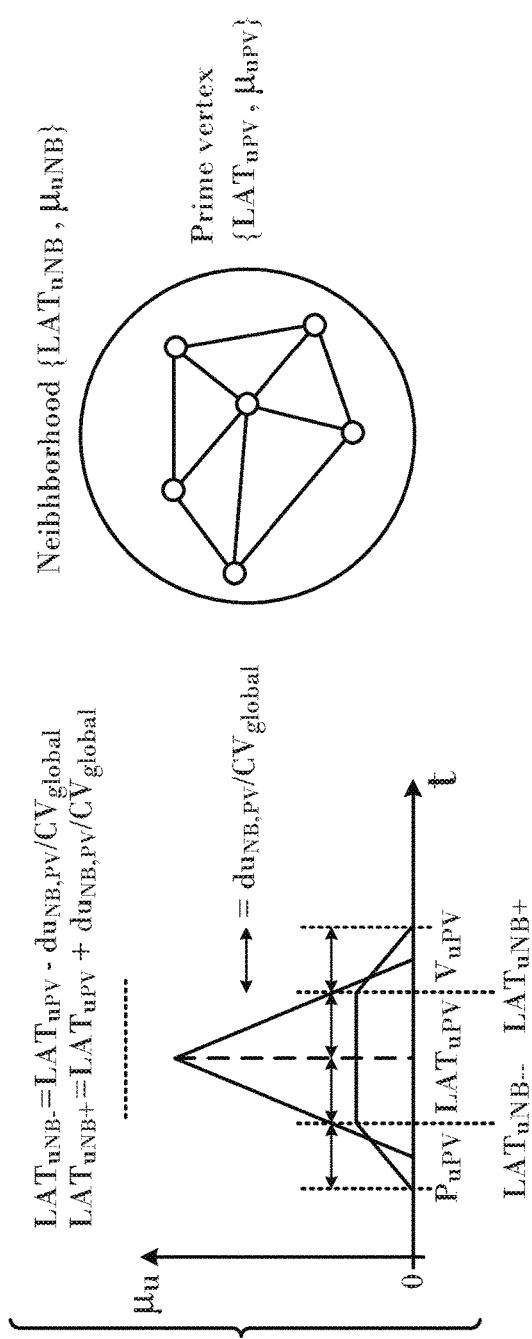
FIG. 25 is a diagram showing development of a neighborhood membership function in a mesh in accordance with an embodiment of the invention.

$\mu_u$ is a fuzzy membership function for the activation at the vertex and is comparable to the function $\mu_e$, on the surface of the mesh, $\mu_u=1$. However, the fuzzy membership function $\mu_u$ is a composite of weighted (denotched) triangular membership functions. Membership functions of neighboring vertices are denotched in terms of distance and conduction velocity of the wave propagating between primary and neighboring vertices as shown in FIG. 25. In order to derive a crisp LAT for a mesh vertex, "defuzzification" is required, e.g., using the conter of gravity (COG) method described below.

Figure 20:
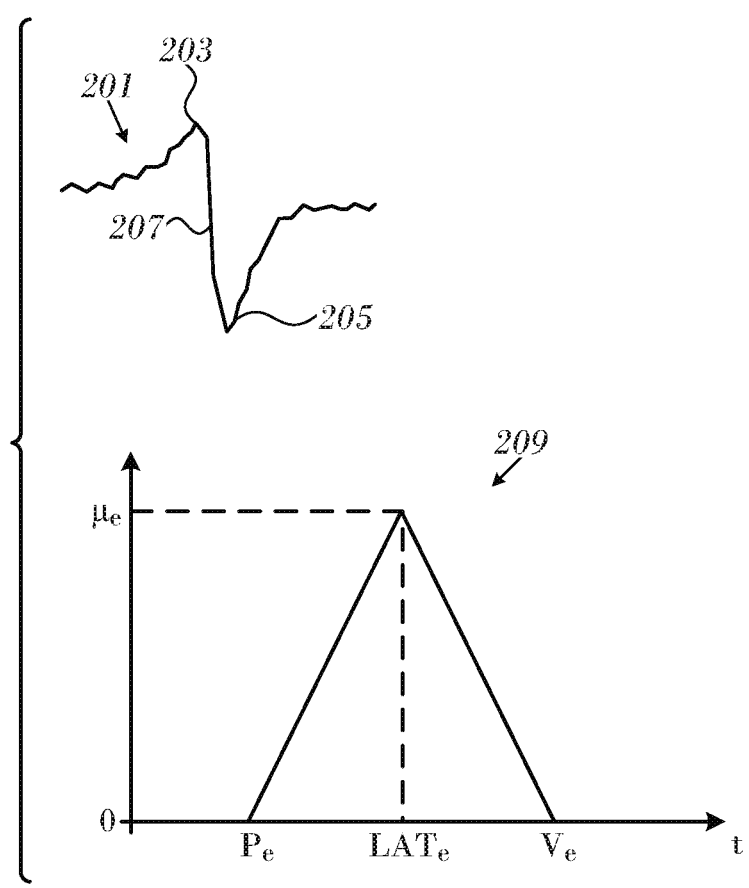
FIG. 20 is a composite diagram illustrating the derivation of fuzzy LATs from an intracardiac electrogram in accordance with an embodiment of the invention.

Reference is now made to FIG. 20, which is a composite diagram illustrating the derivation of fuzzy LATs from an intracardiac electrogram in accordance with an embodiment of the invention. Electrogram 201 has a peak time 203 ($P_e$), a valley time 205 and a mid time 207. A graph 209 of the membership function $\mu_e$ is triangular having a maximum at time $LAT_e$ and zero values at peak and valley times $P_e$ and $V_e$, respectively.

Reference is now made to FIG. 21, which is a composite diagram relating fuzzy LATs to the morphology of an intracardiac electrogram in accordance with an embodiment of the invention. The negative slope of the intracardiac electrogram 211 provides a reference for time window of interest. In intracardiac electrogram 213 a broad propagating fibrillation wave generates a 3 ms slope bounded by broken vertical lines corresponding to peak and valley times $P_e$ and $V_e$, respectively. In graph 215 the maximum membership value max($\mu$) is bound to 1. The area under curve 217 then becomes 1.5.

The morphology of the plot of the function $\mu_e$ can be related to the contact status between the electrodes and the endocardium. Reference is now made to FIG. 22, which is a series of plots of the function $\mu_e$ for electrodes at different distances from the endocardium in accordance with an embodiment of the invention. In graph 219 the electrode is in contact with the endocardium. In graphs 221, 223 the electrodes are located at increasing distances from the endocardium. The curves are increasingly broad and the maximum value of the function $\mu_e$ diminishes as the distance from the endocardium increases.

Figure 23:
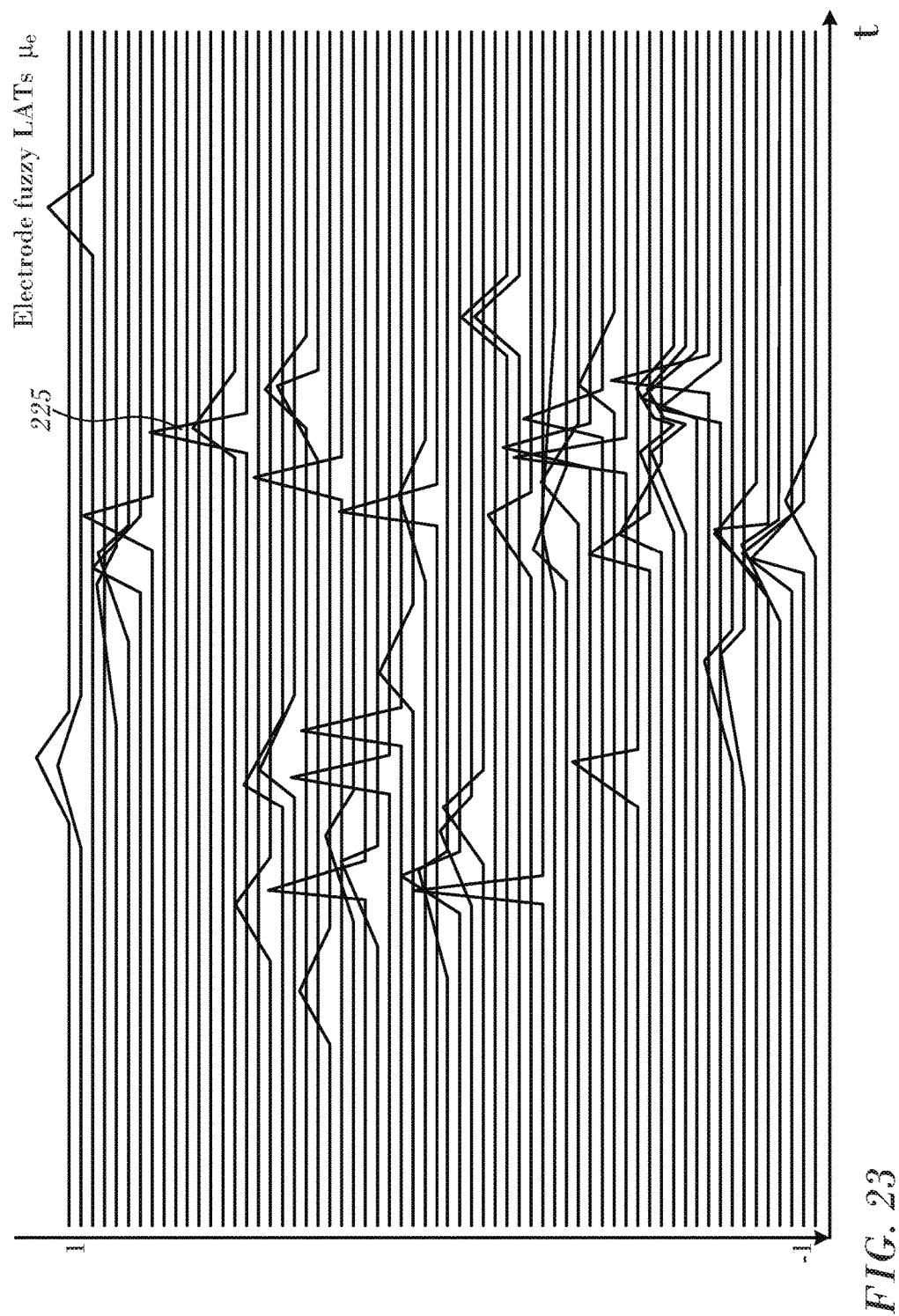
FIG. 23 is a series of plots of the function $\mu_e$ taken from a multi-electrode catheter in accordance with an embodiment of the invention.

Reference is now made to FIG. 23, which is a series of plots of the function $\mu_e$ taken from a multi-electrode catheter in accordance with an embodiment of the invention. Triangles having sharp peaks, e.g., triangle 225, correspond to electrodes that are in contact with the endocardium. Other triangles are not in contact. In general, the greater the width of the base of the triangles and the lower the maximum value of the function, the greater the distance between the electrodes and the endocardium.

The mesh for purposes of fuzzy coherent mapping can be either a catheter electrode mesh, or a mesh that models the cardiac anatomy. For purposes of this disclosure, a "prime vertex" refers to a vertex in the mesh that most closely corresponds to the location of one of the catheter electrodes.

Notation for Fuzzy Coherent Mapping.

Positions of the electrodes in 3D space:

$P_e$ Electrode position.

$S_{pe}$ Set of electrode positions (ne) on mapping array.

Mesh Definition:

$Tu_i$ Mesh Triangles, $1 \le i \le nTu$, nTu Number of Mesh Triangles.

$Vu_j$ Mesh Vertices, $1 \le j \le nVu$, nVu Number of Mesh Vertices.

Mu set of Tu and Vu,

For a mesh vertex:

PV node Prime vertex node;

NB node Neighborhood node

EX node Extrapolated node (Neither a prime vertex node nor a neighborhood node);

Each vertex belongs to one of the following sets:

set a No LAT (EX node), set b Exactly one fuzzy LAT (PV or NB node), set c More than one fuzzy LAT (PV or NB node).

A distance matrix is calculated between electrodes and anatomical mesh vertices:

$D_{eu}$ Distance matrix ($n_u \times n_e$).

Mapping onto Prime Vertices.

Figure 24:
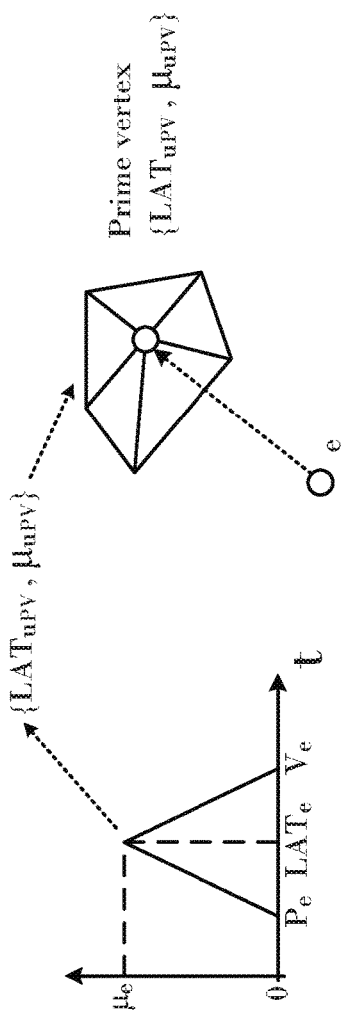
FIG. 24 is a diagram illustrating the mapping of electrode LATs onto a prime vertex of a mesh in accordance with an embodiment of the invention.

Given $D_{eu}$ and $\mu_e$, the contribution of each electrode activation $LAT_e$ is mapped onto the most proximal vertex on the mesh (prime vertex; PV) with maximum truth value $\mu_{uPV}$, as shown in FIG. 24

$LAT_e \rightarrow LAT_{uPV}$; $\mu_e \rightarrow \mu_{uPV}$

Using the membership function, close neighbors around the prime vertices are defined. Neighboring LATs $\mu_u$ are determined by the quantity $d_{uNB,PV}/CV_{global}$ around $LAT_{uPV}$. The direction of activation is not yet known, however. The fuzzy membership function is flat-topped with a width of $2*d_{uNB,PV}/CV_{global}$. This operation is shown in FIG. 25.

Figure 26:
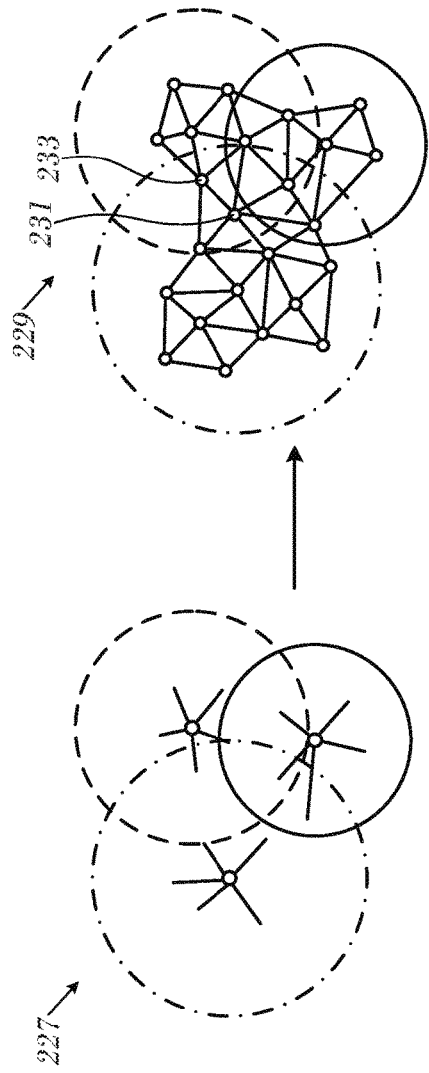
FIG. 26 is a diagram illustrating overlapping of neighborhoods in a mesh in accordance with an embodiment of the invention.

Neighborhoods may overlap, creating more than one fuzzy LAT on mesh vertices. Reference is now made to FIG. 26, which is a diagram illustrating overlapping of neighborhoods in a mesh, in accordance with an embodiment of the invention. At the left of the figure is a group 227 three prime vertices whose neighborhoods are represented by respective circles in which the prime vertices are centered. At the right of the figure is a group 229 in which neighboring vertices of the prime vertices have been defined as described above. Some neighboring vertices, e.g., vertices 231, 233, lie within more than one of the neighborhoods.

Figure 27:
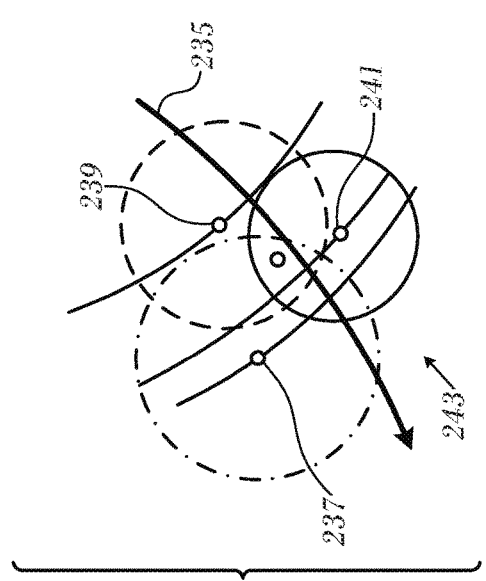
FIG. 27 illustrates mesh neighborhoods and presents two graphs, in accordance with an embodiment of the invention.
Figure 28:
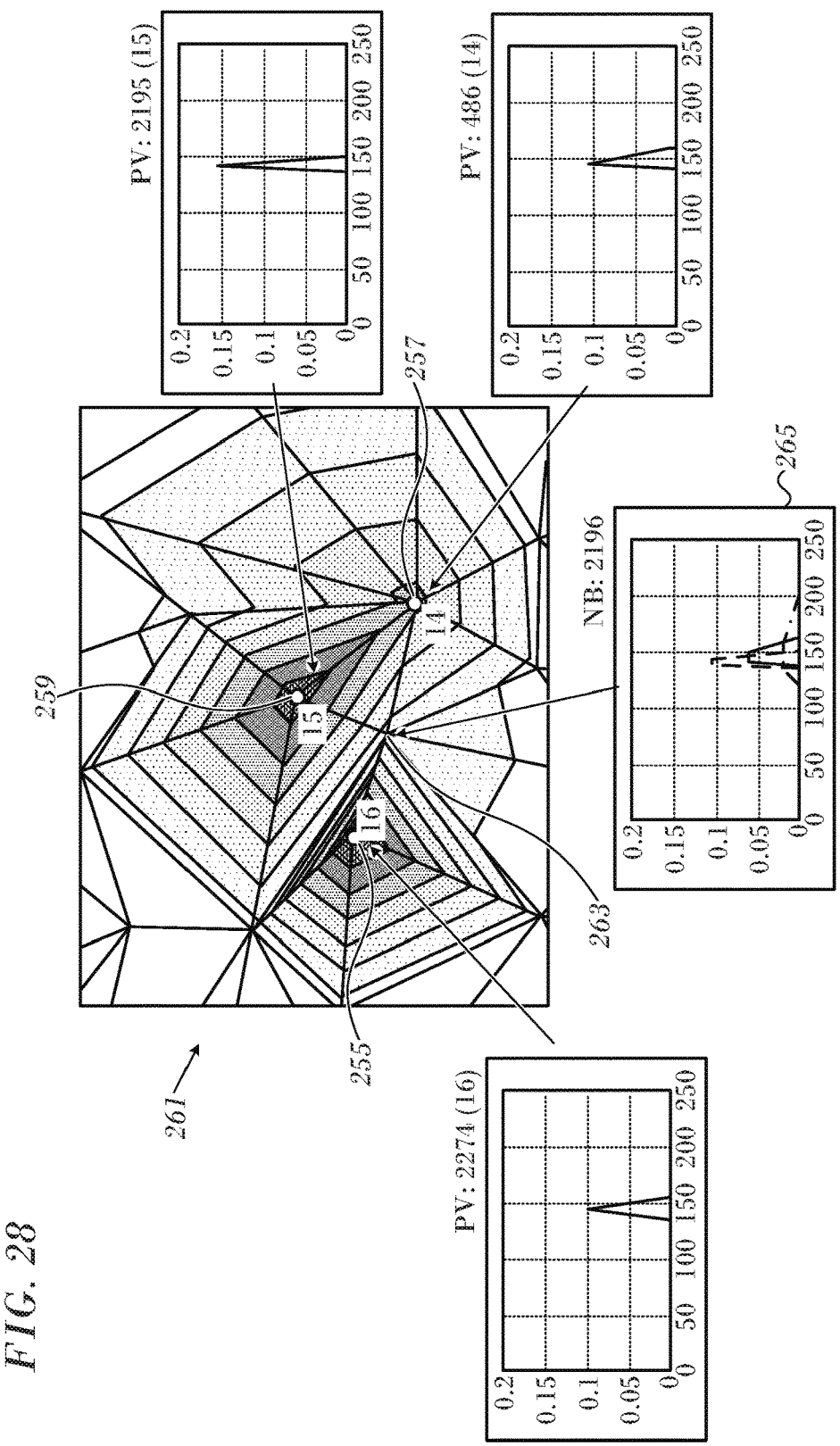
FIG. 28 is a composite diagram illustrating the calculation of a fuzzy LAT in accordance with an embodiment of the invention.

Reference is now made to FIG. 27, which illustrates mesh neighborhoods and presents two graphs in accordance with an embodiment of the invention. This figure illustrates that multiple fuzzy LAT's on mesh vertices may have different truth values. A propagation wave is indicated by arrow 235. Fuzzy LATs 237, 239, 241 lie in a group 243 of three separate neighborhoods and have respective truth values 245, 247, 249 as shown on graph 251. Graph 253 illustrates a membership function that is a composite of weighted, denotched triangular membership function the calculation of a fuzzy LAT for the group 243 using a "center of gravity" (COG) method in which the membership function is divided into two parts such that the areas under the curve are equal Reference is now made to FIG. 28, which is a composite diagram illustrating the calculation of a fuzzy LAT according to the CoG of a group of prime vertices in accordance with an embodiment of the invention. The function $\mu_u$ is shown graphically for three prime vertices 255, 257, 259 as plots, and the function is discretized by zones about the vertices on a pictorial display 261. CoG 263 has a composite plot 265 of the function $\mu_u$ for the vertices 255, 257, 259.

Figure 29:
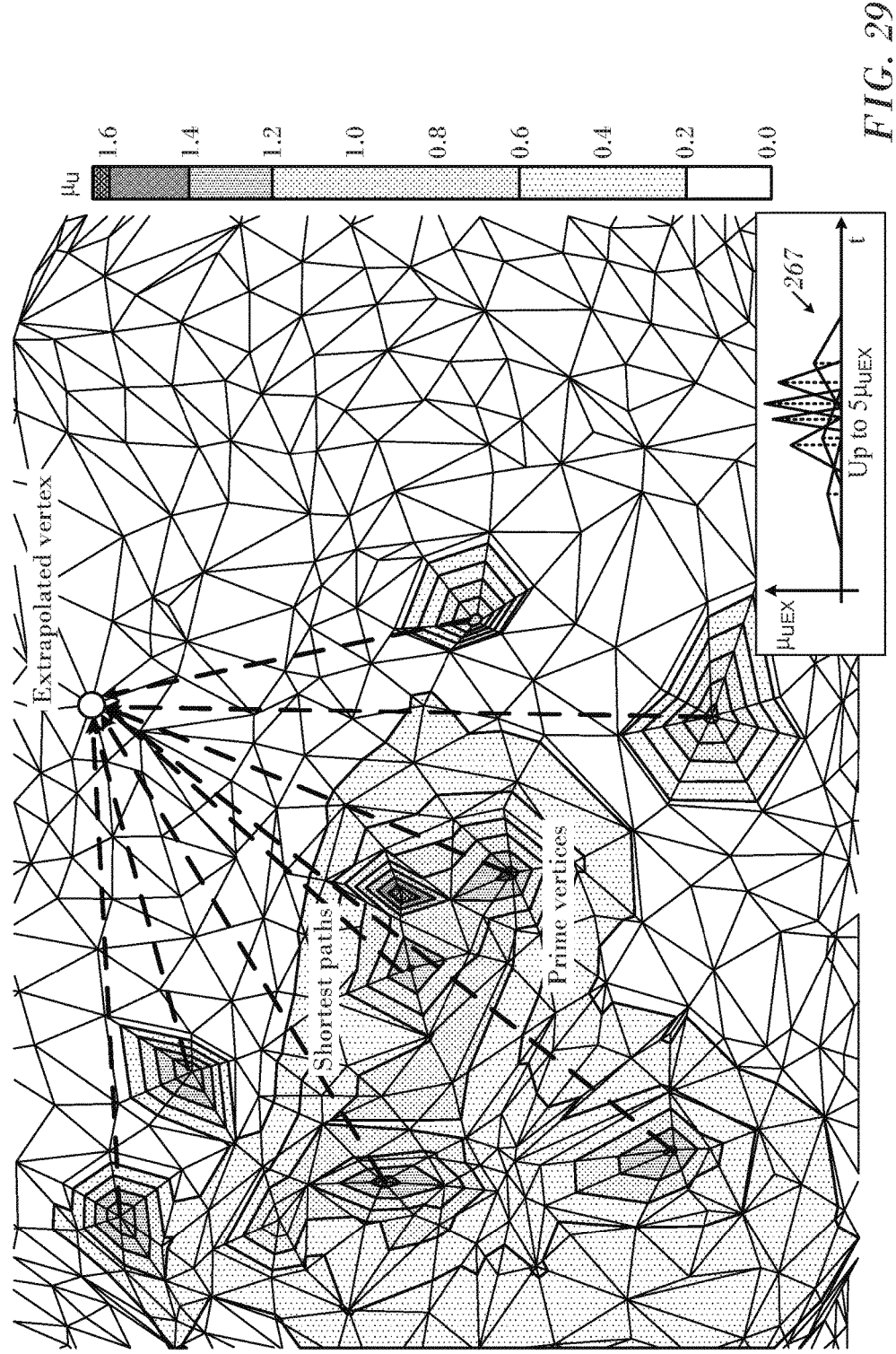
FIG. 29 shows a mesh having an extrapolated vertex in accordance with an embodiment of the invention.

Many vertices (EX nodes) may lack assigned functions $\mu_u$. The values of the function $\mu_u$ for the EX nodes are assigned by evaluation of extrapolated activation waves that pass beneath the prime vertices (PV nodes). Reference is now made to FIG. 29, which shows a mesh having an extrapolated vertex in accordance with an embodiment of the invention. A function $\mu$ is calculated for the vertex as follows:

1. Calculate the shortest distance between the EX node and all prime vertices on the mesh.
2. Calculate the value of the function $\mu_{uEX} = f(\mu_{uPV}, d_{PV, EX})$. This calculation is the same as the initialization of neighboring nodes described above, except that only instances of the function $\mu_{uEX}$ with the five highest truth values are considered, as shown in plot 267.
3. Calculate the fuzzy LAT from the combined function $\mu_{uEX}$ in step 2, using the CoG method.

Optimization of Activation in Fuzzy Coherent Mapping.

Figure 30:
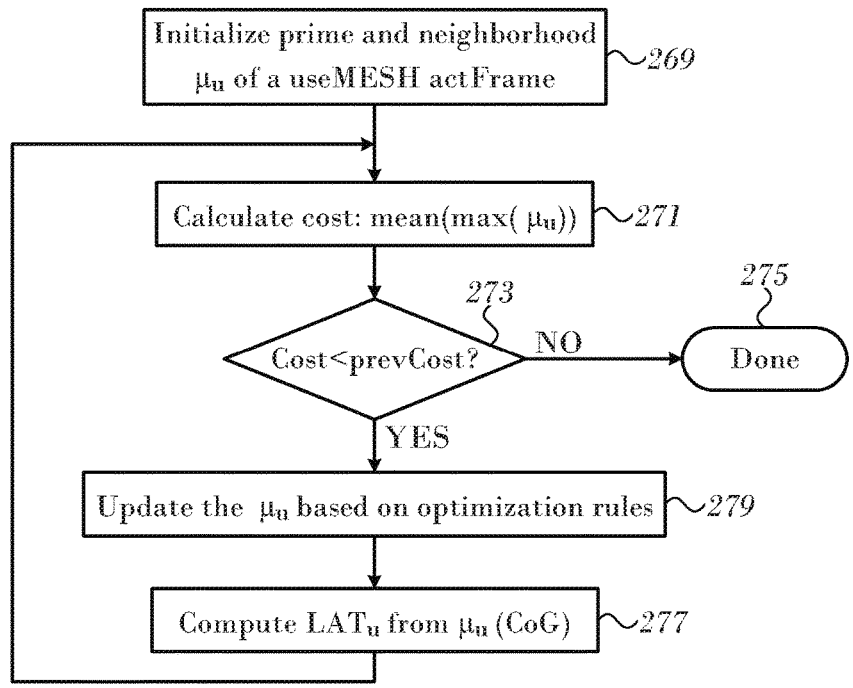
FIG. 30 is a flow chart of a method of optimization of fuzzy activation in accordance with an embodiment of the invention.

Reference is now made to FIG. 30, which is a flow chart of a method of optimization of fuzzy activation in accordance with an embodiment of the invention. In initial step 269 initial values for the function $\mu_u$ are assigned to prime vertices and to neighborhood nodes of an activation frame of a mesh. These procedures have been described above and are not repeated here.

Next, at step 271 a cost function is evaluated. The value of the cost function is the mean of all maximum fuzzy truth values $\mu_u$ for the mesh vertices. This result is increased by decreasing the weighting of the membership functions of proximal vertices.

Next, at decision step 273, it is determined if the cost function in the current iteration is less than that of the previous iteration (within a predefined tolerance). If the determination is negative, then control proceeds to final step 275 and the procedure terminates.

If the determination at decision step 273 is affirmative, then control proceeds to step 277. The values of the function $\mu_u$ are updated based on an optimization procedure that includes minimizing the velocity deviation vector for the current vertex. The procedure is analogous to that described with respect to FIG. 14. The details are not repeated in the interest of brevity. The effect is to maximize uniformity in the conduction of an activation wave, which is travelling at least 0.2 m/s. Such a wave should normally propagate in a continuous manner. Upon completion of step 277 there is a set of fuzzy LATs having respective functions $\mu_u$.

Figure 31:
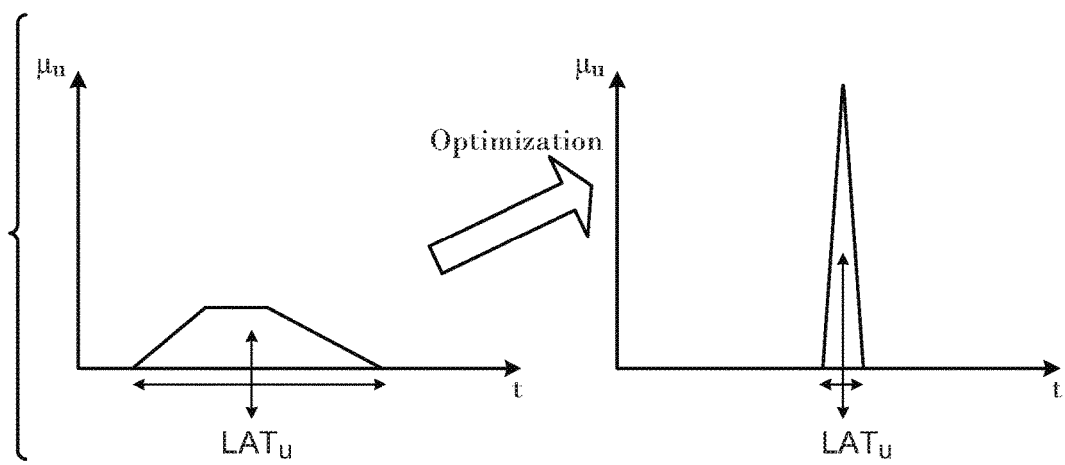
FIG. 31 shows two plots of the function $\mu_u$ in a vertex of a mesh before and after optimization in accordance with an embodiment of the invention.

As the cost function is optimized in successive iterations the value of the function $\mu_u$ increases and its spread decreases, as shown in FIG. 31, which is two plots of the function $\mu_u$ in a vertex of a mesh before and after optimization in accordance with an embodiment of the invention.

Reverting to FIG. 30, next, at step 279 the values $LAT_u$ are computed from the current values of the function $\mu_u$. The procedure then iterates at step 271. Vertices are marked for revision if at least one of the neighboring vertices has $\mu_u > \mu_{u\ min}$. All fuzzy LATs in which the function $\mu_u$ is marked for revision are updated simultaneously at the end of each iteration. In each iterative step the fuzzy LATs at the vertices are adjusted to minimize the angles between the velocity vectors of the surrounding triangles and the mean of these vectors, as described above in the discussion of Equations 1-4. A lower limit is placed on the velocities in order to exclude lines of block.

Figure 32:
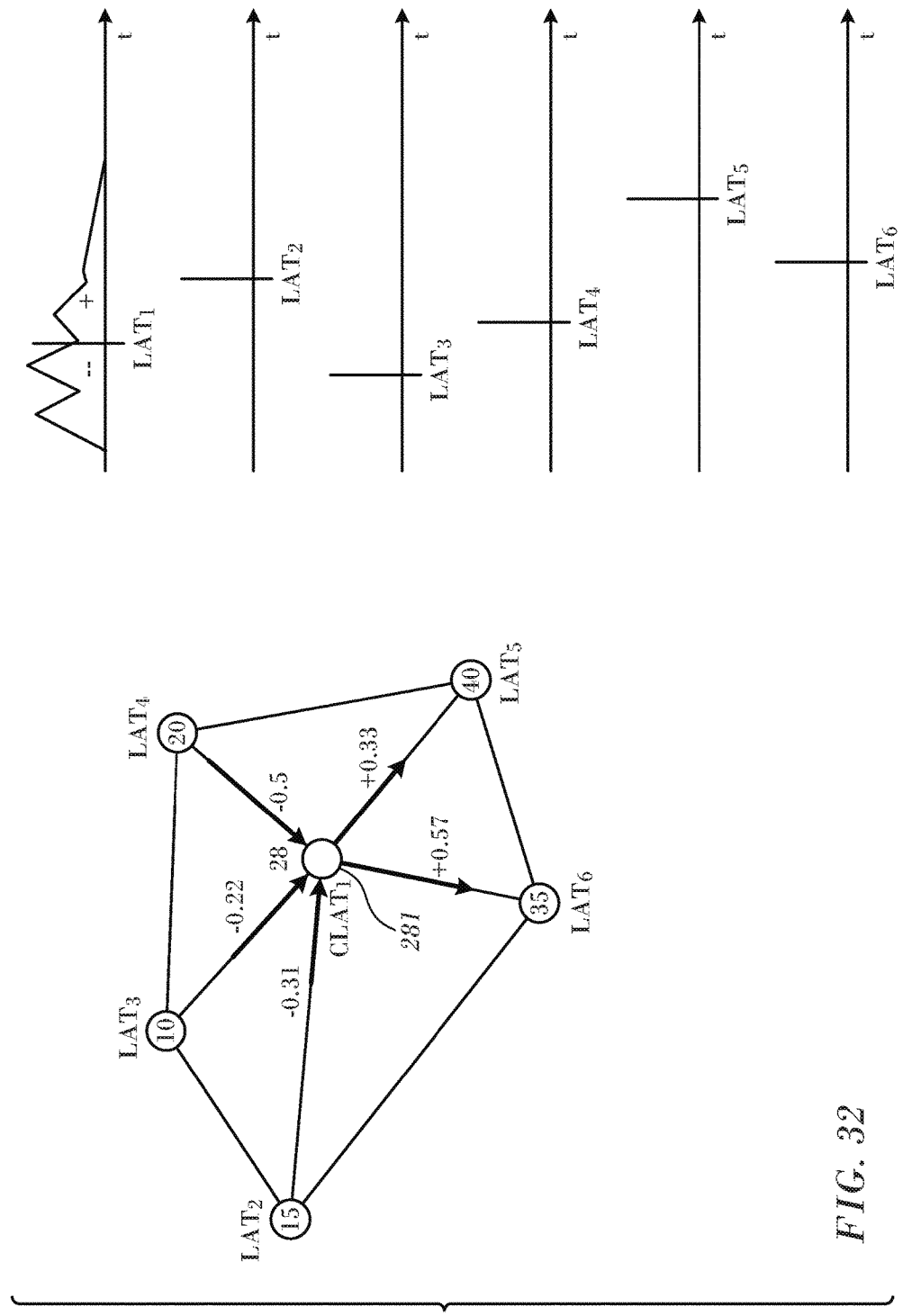
FIG. 32 is a diagram illustrating the optimization of uniform conduction at a center within an area including neighboring vertices in accordance with an embodiment of the invention.

Reference is now made to FIG. 32, which is a diagram illustrating the optimization of uniform conduction at a center within an area including neighboring vertices, in accordance with an embodiment of the invention. The diagram shows a vertex 281 having a fuzzy LAT of 28 ms. Conduction velocities are denoted next to the arrows. Five neighboring vertices with fuzzy LATs ($LAT_2$-$LAT_6$) surround the vertex 281 with respective conduction vectors as shown. In general, when the mean CV is positive, the wave is moving away from a point faster than it is approaching, and the LAT at the CoG ($LAT_1$) must decrease.

Varying the LAT results in rotation of the velocity vectors because of time differences among the triangles. In order to deal with this, the velocity deviation angle is computed by using a step up and step down of the central LAT at the vertex 281. The direction producing the lower difference angle is selected.

Figure 33:
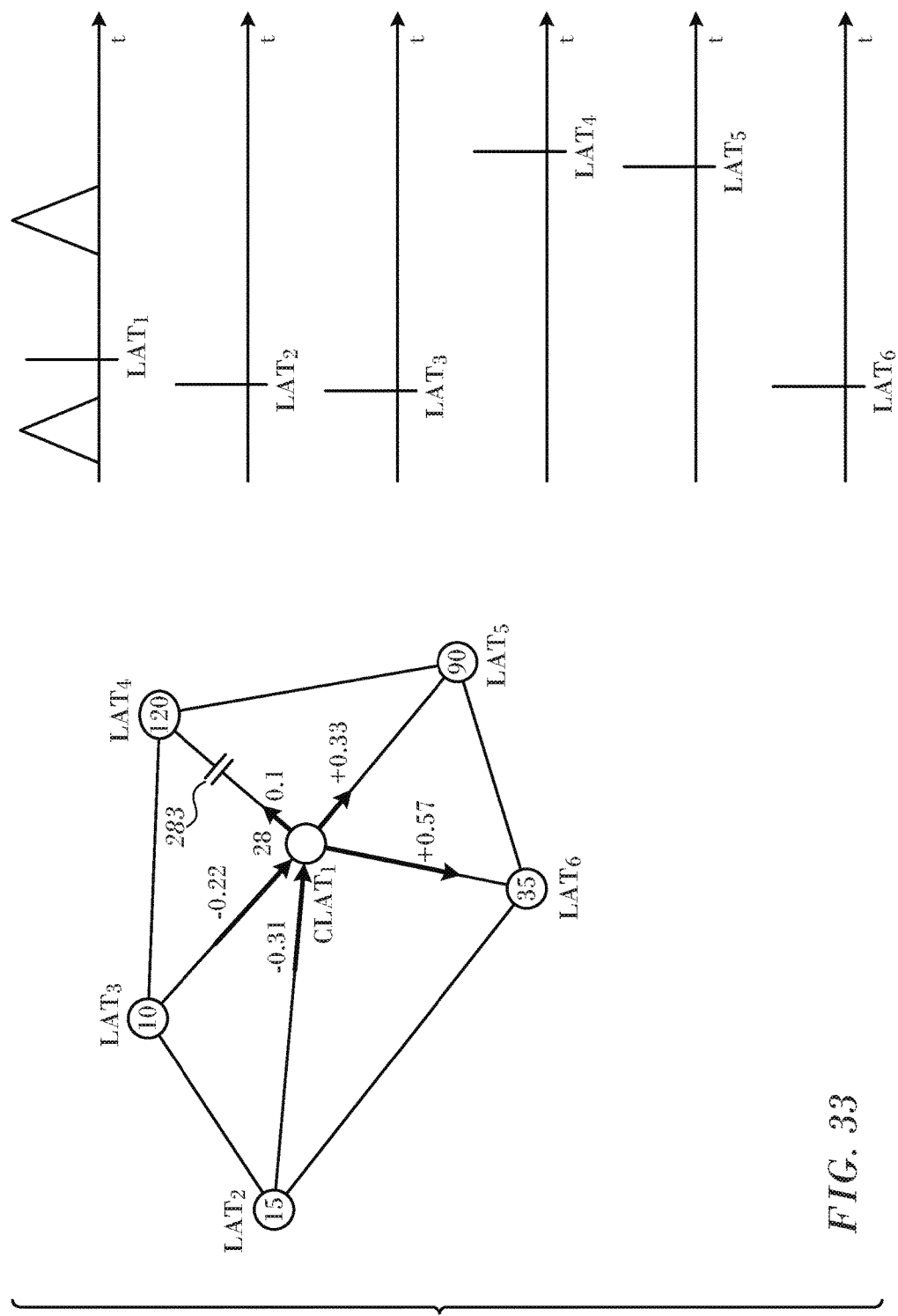
FIG. 33, is a diagram illustrating the optimization of uniform conduction at a center within an area including neighboring vertices in accordance with an embodiment of the invention.

Reference is now made to FIG. 33, which is a diagram similar to FIG. 32, in accordance with an embodiment of the invention. In this example there is a conduction block 283, and the function $\mu_u$ is not updated. Connections between vertices are removed when the conduction velocity is less than a predetermined minimum, after which the algorithm iterates.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method, comprising the acts of:
    inserting a probe into a heart of a living subject, the probe having a plurality of electrodes;
    recording electrograms from the electrodes concurrently at respective locations in the heart, the electrograms comprising readings of the electrodes;
    generating an activation map from the readings, the activation map having fixed local activation times and adjustable local activation times for respective electrodes based on respective readings;

delimiting activation time intervals for respective adjustable local activation times;

transforming the activation map into a map of electrical propagation waves, comprising:

segmenting the electrograms into a series of frames at respective times, wherein each frame includes a matrix comprising assignments of the fixed local activation times and the adjustable local activation times to the respective electrodes;

modeling at least a portion of the heart as a mesh having vertices, each vertex corresponding to location of a respective electrode;

selecting a vertex, the vertex having connected conduction velocities of electrical propagation, wherein at least one of the connected conduction velocity has a respective adjustable local activation time and a respective activation time interval; and determining coherence of the waves at the vertex based on the connected conduction velocities;

maximizing coherence of the waves by adjusting at least one of the adjustable local activation times of the connected conduction velocities to at least one adjusted local activation time within the respective activation time intervals;

reporting the at least one adjusted local activation time;

generating an electroanatomical map with at least one coherent wave based on the at least one adjusted local activation time; and ablating tissue in the heart to modify the electrical propagation waves represented in the electroanatomical map.

2. The method according to claim 1, wherein each activation time interval ranges between a peak and a valley representing a start and an end of a slope of the reading of the respective electrode.

3. The method according to claim 2, wherein the peak and the valley of each activation time interval are ±5 ms of each respective adjustable local activation time.

4. The method according to claim 1, wherein each activation time interval comprises one interval delimited by a peak and a valley representing a start and an end of a slope of the reading of the respective electrode, and another interval comprising a window about the first interval.

5. The method according to claim 1, wherein the window about the one interval is ±40 ms.

6. The method according to claim 1, wherein the fixed and adjustable local activation times are defined by fuzzy electrode membership functions ($\mu_e$) that vary from 0 to 1.

7. The method according to claim 1, wherein maximizing coherence of the waves comprises:

determining a velocity deviation vector at the selected vertex based on the connected conduction velocities; and minimizing a length of the velocity deviation vector.

8. The method according to claim 1, wherein maximizing coherence of the waves comprises:

determining a velocity deviation angle at the selected vertex based on the connected conduction velocities; and minimizing the velocity deviation angle.

9. The method according to claim 1, further comprising interpolating local activation times of the vertices on the mesh that do not correspond to the respective locations of the electrodes.

10. The method according to claim 1, wherein the local activation times at the vertices of the mesh are represented as fuzzy vertex membership functions ($\mu_v$) that vary between 0 and 1, the vertex membership functions at each of the vertices comprising weighted combinations of the vertex membership functions of neighboring vertices thereof.

11. The method according to claim 10, wherein maximizing coherence of the waves comprises adjusting the one or more adjustable local activation times of the connected conduction velocities of the selected vertex of the mesh representing the location of the respective electrode to maximize an average value of the vertex membership functions in the mesh.

12. The method according to claim 10, further comprising assigning vertex membership functions to non-neighboring vertices of the mesh by extrapolation.

13. An apparatus, comprising:

a probe having a plurality of electrodes and adapted for insertion into a heart of a living subject; and a processor configured to receive electrical signals from the electrodes and to perform the acts of:

recording electrograms from the electrodes concurrently at respective locations in the heart, the electrograms comprising readings of the electrodes;

generating an activation map from the readings, the activation map having fixed local activation times and adjustable local activation times for respective electrodes based on respective readings;

delimiting activation time intervals for respective adjustable local activation times;

transforming the activation map into a map of electrical propagation waves, comprising:

segmenting the electrograms into a series of frames at respective times, wherein each frame includes a matrix comprising assignments of the fixed local activation times and the adjustable local activation times to the respective electrodes;

modeling at least a portion of the heart as a mesh having vertices, each vertex corresponding to location of a respective electrode;

selecting a vertex, the vertex having connected conduction velocities of electrical propagation, wherein at least one of the connected conduction velocity has a respective adjustable local activation time and a respective activation time interval; and determining coherence of the waves at the vertex based on the connected conduction velocities;

maximizing coherence of the waves by adjusting at least one of the adjustable local activation times of the connected conduction velocities to at least one adjusted local activation time within the respective activation time intervals;

reporting the at least one adjusted local activation time;

generating an electroanatomical map with at least one coherent wave based on the at least one adjusted local activation time; and an ablation power generator connected to the probe for ablating tissue in the heart to modify the electrical propagation waves represented in the electroanatomical map.

14. The apparatus according to claim 13, wherein each activation time interval ranges between a peak and a valley representing a start and an end of a slope of the reading of the respective electrode.

15. The apparatus according to claim 14, wherein the peak and the valley are ±5 ms of each respective adjustable local activation time.

16. The apparatus according to claim 14, wherein each activation time interval comprises one interval delimited by a peak and a valley representing a start and an end of a slope of the reading of the respective electrode, and another interval comprising a window about the first interval, wherein adjusting the adjustable local activation time is performed within the one interval.

17. The apparatus according to claim 16, wherein the window about the one interval is ±40 ms.

18. The apparatus according to claim 13, wherein the fixed and adjustable local activation times are defined by fuzzy electrode membership functions (µe) that vary from 0 to 1.

19. The apparatus according to claim 13, wherein maximizing coherence of the waves comprises:
determining a velocity deviation vector at the selected vertex based on the connected conduction velocities; and
minimizing a length of the velocity deviation vector.

20. The apparatus according to claim 13, wherein maximizing coherence of the waves comprises:
determining a velocity deviation angle at the selected vertex based on the connected conduction velocities; and
minimizing the velocity deviation angle.

21. The apparatus according to claim 13, further comprising interpolating local activation times of the vertices on the mesh that do not correspond to the respective locations of the electrodes.

22. The apparatus according to claim 13, wherein the local activation times at the vertices of the mesh are represented as fuzzy vertex membership functions (µu) that vary between 0 and 1, the vertex membership functions at each of the vertices comprising weighted combinations of the vertex membership functions of neighboring vertices thereof.

23. The apparatus according to claim 22, wherein maximizing coherence of the waves comprises adjusting the one or more adjustable local activation times of the connected conduction velocities of the selected vertex of the mesh representing the location of the second electrode to maximize an average value of the vertex membership functions in the mesh.

24. The apparatus according to claim 22, further comprising assigning vertex membership functions to non-neighboring vertices of the mesh by extrapolation.

\* \* \* \* \*